(12) United States Patent
Laugharn, Jr. et al.

(10) Patent No.: US 8,991,259 B2
(45) Date of Patent: Mar. 31, 2015

(54) METHOD AND SYSTEM FOR ACOUSTICALLY TREATING MATERIAL

(71) Applicant: Covaris, Inc., Woburn, MA (US)

(72) Inventors: James A. Laugharn, Jr., Winchester, MA (US); Xiaoyin He, Waltham, MA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 13/891,659

(22) Filed: May 10, 2013

(65) Prior Publication Data

US 2013/0244242 A1    Sep. 19, 2013

Related U.S. Application Data

(63) Continuation of application No. 12/914,370, filed on Oct. 28, 2010, now Pat. No. 8,459,121.

(51) Int. Cl.
*G01N 29/28* (2006.01)
*B01F 11/02* (2006.01)
*B01J 19/10* (2006.01)
(Continued)

(52) U.S. Cl.
CPC ............ *B01J 19/10* (2013.01); *B01F 11/0283* (2013.01); *B01J 19/006* (2013.01); *B01J 19/008* (2013.01); *B01J 19/245* (2013.01); *B01F 11/02* (2013.01); *A61L 2/025* (2013.01); *C12N 13/00* (2013.01); *B01F 3/08* (2013.01); *B01F 3/12* (2013.01);
(Continued)

(58) Field of Classification Search
USPC .................. 73/632, 644, 64.53; 422/20, 128; 366/127; 435/6.12, 173.8, 289.1, 435/306.1, 91.2
See application file for complete search history.

(56) References Cited

U.S. PATENT DOCUMENTS 1,734,975 A    11/1929 Loomis
2,447,061 A    8/1948 Franklin
(Continued)

FOREIGN PATENT DOCUMENTS

DE          952 707 C      11/1956
EP        1 925 359 A1      5/2008
WO    WO 2007/016605 A2    2/2007

OTHER PUBLICATIONS

International Search Report and Written Opinion for International Application No. PCT/US2011/058320 mailed Feb. 29, 2012.
(Continued)

*Primary Examiner* — J M Saint Surin
(74) *Attorney, Agent, or Firm* — Wolf, Greenfield & Sacks, P.C.

(57) ABSTRACT

Methods and systems for acoustically treating material using a continuous process in which material may be caused to flow in a continuous or intermittent fashion into/out of an acoustic treatment chamber where the material is exposed to focused acoustic energy. The methods and systems may be arranged to permit continuous processing for extended periods while an acoustic energy source operates at a relatively high power output. Treatment chambers may include features such as an acoustic window, a heat exchanger, inlet/outlet flow arrangements, an inspection window, insert elements that define a treatment volume size or shape, etc. Treatment system configurations relating to arrangements of a treatment chamber relative to an acoustic source and coupling medium, material flow paths, and others are provided.

29 Claims, 5 Drawing Sheets

(51) Int. Cl.
*B01J 19/00* (2006.01)
*B01J 19/24* (2006.01)
*A61L 2/025* (2006.01)
*C12N 13/00* (2006.01)
*B01F 3/08* (2006.01)
*B01F 3/12* (2006.01)

(52) U.S. Cl.
CPC *B01F 2215/0037* (2013.01); *B01J 2219/00094* (2013.01)
USPC ............ 73/644; 73/64.53; 366/108; 435/6.12

(56) References Cited

U.S. PATENT DOCUMENTS

| | | | |
|---|---|---|---|
| 2,565,159 A | 8/1951 | Williams | |
| 2,578,505 A | 12/1951 | Carlin | |
| 2,632,634 A | 3/1953 | Williams | |
| 2,738,172 A | 3/1956 | Spiess et al. | |
| 2,855,526 A | 10/1958 | Jones | |
| 2,864,592 A | 12/1958 | Camp | |
| 2,916,265 A | 12/1959 | Towne | |
| 2,950,725 A | 8/1960 | Jacke et al. | |
| 3,066,686 A | 12/1962 | O'Neill | |
| 3,194,640 A | 7/1965 | Nesh | |
| 3,292,910 A | 12/1966 | Martner | |
| 3,396,286 A | 8/1968 | Anderson et al. | |
| 3,481,186 A | 12/1969 | Cellitti et al. | |
| 3,614,069 A | 10/1971 | Murry | |
| 3,743,523 A | 7/1973 | Bodine | |
| 3,807,704 A | 4/1974 | Janzen | |
| 3,837,805 A | 9/1974 | Boucher | |
| 3,876,890 A | 4/1975 | Brown | |
| 4,028,933 A | 6/1977 | Lemons | |
| 4,307,964 A | 12/1981 | Dudgeon et al. | |
| RE31,779 E | 12/1984 | Alliger | |
| 4,488,816 A | 12/1984 | Vota | |
| 4,541,281 A | 9/1985 | Chubachi | |
| 4,571,087 A | 2/1986 | Ranney | |
| 4,644,808 A | 2/1987 | Lecoffre | |
| 4,764,905 A | 8/1988 | Granz et al. | |
| 4,834,124 A | 5/1989 | Honda | |
| 4,862,060 A | 8/1989 | Scott et al. | |
| 4,879,011 A | 11/1989 | Schram | |
| 4,889,122 A | 12/1989 | Watmough et al. | |
| 4,926,871 A | 5/1990 | Ganguli et al. | |
| 4,983,189 A | 1/1991 | Peterson et al. | |
| 5,026,167 A | 6/1991 | Berliner | |
| 5,037,481 A | 8/1991 | Bran | |
| 5,307,680 A * | 5/1994 | Drescher-Krasicka | ......... 73/606 |
| 5,395,592 A | 3/1995 | Bolleman et al. | |
| 5,484,573 A | 1/1996 | Berger et al. | |
| 5,523,058 A | 6/1996 | Umemura et al. | |
| 5,549,003 A * | 8/1996 | Drescher-Krasicka | ......... 73/606 |
| 5,623,095 A | 4/1997 | Beller | |
| 5,631,425 A | 5/1997 | Wang et al. | |
| 5,639,423 A | 6/1997 | Northrup et al. | |
| 5,681,396 A | 10/1997 | Madanshetty | |
| 5,688,406 A | 11/1997 | Dickinson et al. | |
| 5,736,100 A | 4/1998 | Miyake et al. | |
| 5,740,794 A | 4/1998 | Smith et al. | |
| 5,759,162 A | 6/1998 | Oppelt et al. | |
| 5,779,985 A | 7/1998 | Sucholeiki | |
| 5,803,099 A | 9/1998 | Sakuta et al. | |
| 5,831,166 A | 11/1998 | Kozuka et al. | |
| 5,834,648 A | 11/1998 | Wang et al. | |
| 5,890,802 A | 4/1999 | Evensen | |
| 5,993,671 A | 11/1999 | Peltzer | |
| 6,003,388 A | 12/1999 | Oeftering | |
| 6,010,316 A | 1/2000 | Haller et al. | |
| 6,039,309 A | 3/2000 | Kuklinski | |
| 6,042,556 A | 3/2000 | Beach et al. | |
| 6,086,821 A | 7/2000 | Lee | |
| 6,100,084 A | 8/2000 | Miles et al. | |
| 6,210,128 B1 | 4/2001 | Rife et al. | |
| 6,224,778 B1 | 5/2001 | Peltzer | |
| 6,244,738 B1 | 6/2001 | Yasuda et al. | |
| 6,277,332 B1 | 8/2001 | Sucholeiki | |
| 6,284,113 B1 | 9/2001 | Bjornson et al. | |
| 6,291,180 B1 | 9/2001 | Chu | |
| 6,361,747 B1 | 3/2002 | Dion et al. | |
| 6,413,783 B1 | 7/2002 | Wohlstadter et al. | |
| 6,440,725 B1 | 8/2002 | Pourahmadi et al. | |
| 6,515,030 B1 | 2/2003 | Bechtel et al. | |
| 6,699,711 B1 | 3/2004 | Hahn et al. | |
| 6,719,449 B1 | 4/2004 | Laughram et al. | |
| 6,737,021 B2 | 5/2004 | Watari et al. | |
| 6,948,843 B2 | 9/2005 | Laugharn et al. | |
| 7,521,023 B2 | 4/2009 | Laugharn et al. | |
| 7,686,500 B2 * | 3/2010 | Laugharn et al. | ............. 366/127 |
| 7,687,026 B2 * | 3/2010 | Laugharn et al. | .................. 422/3 |
| 7,981,368 B2 * | 7/2011 | Laugharn et al. | ............. 422/128 |
| 8,196,658 B2 | 6/2012 | Miller et al. | |
| 8,263,005 B2 * | 9/2012 | Laugharn et al. | ............. 422/128 |
| 2006/0158956 A1 | 7/2006 | Laugharn et al. | |
| 2009/0317884 A1 | 12/2009 | Laugharn et al. | |
| 2012/0234625 A1 | 9/2012 | Laugharn et al. | |

OTHER PUBLICATIONS

International Preliminary Report on Patentability for International Application No. PCT/US2011/058320 mailed May 10, 2013.

* cited by examiner

METHOD AND SYSTEM FOR ACOUSTICALLY TREATING MATERIAL

RELATED APPLICATIONS

This application is a continuation of U.S. patent application Ser. No. 12/914,370 filed Oct. 28, 2010, entitled "METHOD AND SYSTEM FOR ACOUSTICALLY TREATING MATERIAL" the contents of which is incorporated herein by reference in its entirety.

BACKGROUND

1. Field of Invention

The present invention generally relates to the field of controlled sonic energy emitting devices for treating material, particularly systems involving material flowing past or through a 'processing zone'.

2. Related Art

Ultrasonics have been utilized for many years for a variety of diagnostic, therapeutic, and research purposes. The acoustic physics of ultrasonics is well understood; however, the biophysical, chemical, and mechanical effects are generally only empirically understood. Some uses of sonic or acoustic energy in materials processing include "sonication," an unrefined process of mechanical disruption involving the direct immersion of an unfocused ultrasound source emitting energy in the kilohertz ("kHz") range into a fluid suspension of the material being treated. Accordingly, the sonic energy often does not reach a target in an effective dose because the energy is scattered, absorbed, and/or not properly aligned with the target. Sonication has also hit limits on effectiveness when applied to higher sample volumes or continuous process streams. There are also specific clinical examples of the utilization of therapeutic ultrasound (e.g., lithotripsy) and of diagnostic ultrasound (e.g., fetal imaging). However, ultrasonics have heretofore not been controlled to provide an automated, broad range, precise materials processing or reaction control mechanism. In U.S. Pat. No. 7,521,023 and others, the use of 'focused acoustical energy' is described to overcome some of the limitations of traditional 'sonication.' Focusing the acoustical energy has many advantages, and can be effective at processing high sample volumes or continuous process streams through the use of a "processing chamber" through which the sample material passes.

SUMMARY OF INVENTION

The present invention relates to systems and methods for scaling a process utilizing focused acoustical energy to larger volume batch and continuous process flows, such that the desired result of acoustic treatment can be achieved on larger sample volumes. The desired result of acoustic treatment, which may be achieved or enhanced by use of ultrasonic wavetrains, can be without limitation, heating the sample, cooling the sample, fluidizing the sample, micronizing the sample, mixing the sample, stirring the sample, disrupting the sample, permeabilizing a component of the sample, forming a nanoemulsion or nano formulation, enhancing a reaction in the sample, solubilizing, sterilizing the sample, lysing, extracting, comminuting, catalyzing, and selectively degrading at least a portion of a sample. Sonic waves may also enhance filtration, fluid flow in conduits, and fluidization of suspensions. Processes of the invention may be synthetic, analytic, or simply facilitative of other processes such as stirring.

For example, altering the permeability or accessibility of a material in a controlled manner can allow for manipulation of the material while preserving the viability and/or biological activity of the material. In another example, mixing materials or modulating transport of a component into or out of materials, in a reproducible, uniform, and automated manner, can be beneficial. According to one embodiment of the system, sample processing control includes a feedback loop for regulating at least one of sonic energy location, pulse pattern, pulse intensity, duration, and absorbed dose of the ultrasound to achieve the desired result of acoustic treatment. In one embodiment, the ultrasonic energy is in the megahertz (MHz) frequency range, in contrast to classical sonic processing which typically employs ultrasonic energy in the kilohertz (kHz) frequency range.

In prior systems, when unfocused, and uncontrolled ultrasonic energy interacts with a complex biological or chemical system, the acoustic field often becomes distorted, reflected, and defocused. The net effect is that energy distribution becomes non-uniform and/or defocused compared to the input. Non-uniform reaction conditions can limit reaction applications to non-critical processes, such as bulk fluid treatment where temperature gradients within a sample are inconsequential. However, some of the non-uniform aspects are highly deleterious to samples, such as extreme temperature gradients that damage sample integrity. For example, in some instances, high temperatures generated would irreversibly denature target proteins. As another example, when improperly controlled ultrasound is applied to a bulk biological sample solution, such as for the extraction of intracellular constituents from tissue, the treatment causes a complex, heterogeneous, mixture of sub-events that vary during the course of a treatment dose. For example, the energy may spatially displace a target moiety and shift the target out of the optimal energy zone. Additionally or alternatively, the energy may result in interference that reflects the acoustic energy. For example, a "bubble shield" occurs when a wave front of sonic energy creates cavitation bubbles that persist until the next wave front arrives, such that the energy of the second wave front is at least partially blocked and/or reflected by the bubbles. Still further, larger particles in the sample may move to low energy nodes, thereby leaving the smaller particles in the sample with more dwell-time in the high energy nodes. In addition, the sample viscosity, temperature, and uniformity may vary during the ultrasonic process, resulting in gradients of these parameters during processing. Accordingly, current processes are generally random and non-uniform, especially when applied to in vitro applications, such as membrane permeabilization, hindering the use of ultrasound in high throughput applications where treatment standardization from one sample to the next is required. As a consequence, many potential applications of ultrasound, especially biological applications, are limited to specific, highly specialized applications, such as lithotripsy and diagnostic imaging, because of the potentially undesirable and uncontrollable aspects of ultrasound in complex systems.

The use of focused acoustical energy, as described in U.S. Pat. No. 7,521,023 (which is incorporated herein by reference in its entirety) and others, can overcome these limitations, and methods for acoustic treatment of a sample in an enclosed vessel are disclosed. Processing of sample material volumes greater than that of a single vessel can be achieved by transfer of the material into, and out of a focused acoustical 'process zone' or 'reaction chamber'. The material may be resident in the processing zone until the desired result is achieved (single pass), and then transferred to downstream process steps, or captured as a finished product.

The present invention addresses the problem of scaling the application of focused ultrasonic energy to treat larger volumes of material, including continuous processes as well as batch scale processing, and provides apparatus and methods for the non-contact treatment of samples with ultrasonic energy using a focused beam of energy. The frequency of the beam can be variable, can be in the range of about 100 kHz to 100 MHz, more preferably 500 kHz to 10 MHz, and can be focused to a processing zone of approximately 10 mm to 20 mm (and possibly of larger size with increases in energy), with the sample material passing through this zone to achieve the desired effect. For example, some embodiments of the present invention can treat samples with ultrasonic energy while controlling the temperature of the sample, by use of computer-generated complex wave trains, which may further be controlled by the use of feedback from a sensor. The acoustic output signal, or wave train, can vary in any or all of frequency, intensity, duty cycle, burst pattern, and pulse shape. Moreover, this treatment can be undertaken automatically under computer control, and can also be linked to instrumentation and measurement feedback from the bulk or output stream. In another example, some embodiments of the present invention can treat samples with ultrasonic energy by relative movement of the sample and the focus of the beam, in any or all of two or three dimensions, to ensure complete and thorough mixing within the processing zone.

In some embodiments, material can be processed in a chamber that is sealed and has one or more inlets and outlets to the chamber for effective transfer of the bulk fluid material through the chamber. The chamber can be sealed during the treatment to prevent contamination of the sample material or of the environment. In some embodiments, arrays of chambers can be used for processing multiple sample streams in parallel, where very large sample volumes are needed, such as in manufacturing process streams. In some embodiments, the chambers and/or other components that contact a material processed may be made in a disposable form, e.g., for one time use in processing a material and discarded thereafter.

The sample container can be a chamber comprised of one or more pieces and may include an acoustic 'window' through which the sonic energy passes. This window can be made from a variety of materials to optimize the desired effect, and can include glass, thin film polymers such as polyimide, other moldable polymers, quartz, sapphire and other materials. The chamber can have one or more inlets and one or more outlets for transfer of material into or out of the chamber. The rate at which material is transferred through the chamber can be controlled actively via a pumping system, such as a peristaltic, gear, or other pump, or passively via gravity fed methods such as elevation changes or tilting a chamber through an oscillation about its axis. The apparatus can also include an acoustically transparent material disposed between the sonic energy source and the holder. The sonic energy source can generate sonic energy at two or more different frequencies, optionally in the form of a serial wavetrain. The wavetrain can include a first wave component and a different second wave component. Alternatively or additionally, the wavetrain can include about 1000 cycles per burst at about a 10% duty cycle at about a 500 mV amplitude.

In one illustrative embodiment, a system for treating a material with acoustic energy includes a chamber defining an internal volume and having an opening into the internal volume. An inlet is arranged to provide an inflow of material into the internal volume and an outlet is arranged to discharge an outflow of material from the internal volume. In some arrangements, the inlet and/or outlet may be have a check valve or otherwise be arranged to help influence flow in the internal volume, e.g., help ensure that flow, though potentially intermittent, is maintained in a direction from the inlet to the outlet. A window in the opening of the chamber may be arranged to sealingly close the opening and to transmit focused acoustic energy into the chamber for treatment of material in the internal volume. The window may be generally transparent to acoustic energy having a frequency of about 100 kHz to 100 MHz. In this way, the window may minimally impede the acoustic energy traveling into the internal volume. In some arrangements, the window may help direct the acoustic energy, e.g., the window may have a convex face or other arrangement that has a focusing or lens affect on the acoustic energy. An acoustic energy source, such as one or more piezoelectric transducers, may be spaced from the window and be arranged to emit acoustic energy having a frequency of about 100 kHz to 100 MHz so as to create a focal zone of acoustic energy in the internal volume. The system may be arranged to accommodate continuous acoustic treatment of material in the chamber for an extended time period, e.g., for 1 hour or more, at a relatively high intensity, e.g., at an output of the acoustic transducer of 200 watts or more, without experiencing excessive heat buildup or other problems. (In a continuous acoustic treatment, material may be caused to flow in a continuous fashion in a chamber, or may flow in an intermittent fashion. Also, the acoustic energy source may operate at a power level that varies, but on a time averaged basis operates at a relatively high power output level, e.g., 200 watts or more) This is in contrast to prior acoustic treatment arrangements in which continuous acoustic treatment for 1 hour or more could not have been achieved for a variety of different reasons, such as excessive heat buildup, failure of the acoustic source, damage to the sample material, and so on.

In some arrangements, the internal volume may be suitably sized or otherwise arranged to help expose material in the internal volume to the acoustic energy. For example, the internal volume may include walls that are located near the boundaries of an acoustic focal zone in the internal chamber to help ensure that material is maintained in or near the focal zone during treatment. In other arrangements, the internal volume may include elements that provide nucleation points for cavitation or other acoustically-caused affects. A coupling medium, which may be liquid or solid, may be arranged to transmit acoustic energy from the acoustic energy source to the window. For example, a water bath may be positioned between the acoustic energy source and the window of the chamber. In some arrangements, the chamber may be partially or completely submerged in a liquid coupling medium, such as water.

In one illustrative embodiment, the chamber and window may be arranged to maintain a pressurized environment in the internal volume. Providing a suitable pressure in the internal volume may help enhance reaction rates, may help reduce cavitation, or provide other desirable affects in the acoustic treatment. The chamber may include a second window, e.g., on an upper surface of the chamber opposite the window, that permits visual inspection of the internal chamber. For example, a sensor, such as a video camera or other optical sensor, may capture images of the internal chamber during treatment. The image data may be used to control operation of the system, such as material flow rates, acoustic energy properties, etc., to achieve desired results. For example, image analysis techniques may be used on the image data to detect treatment characteristics, such as cavitation bubble presence or size, material flow rates, mixing rates, etc., and/or material characteristics, such as particle size, homogenization, fluidization, etc., which are used to control the acoustic source or other aspects of the system.

In one embodiment, the chamber may include a heat exchanger at an outer surface arranged to exchange heat with the coupling medium. For example, the heat exchanger may include a plurality of radial fins, rods, recesses, cavities or other features that help to transfer heat with respect to the internal volume of the chamber. In some arrangements, heat may be transferred into the internal volume, whereas in other arrangements, heat may be transferred out of the internal volume, at least in part, by the heat exchanger. A temperature of a coupling medium, whether the acoustic coupling medium or other thermal coupling medium, may be controlled to affect desired heat transfer. An electric resistance heater or other heat generator may be provided with the chamber to provide an additional heat source, if desired. In another embodiment, the heat exchanger may include a heating or cooling jacket associated with at least a portion of the chamber to deliver heating/cooling fluid to a wall of the chamber. The jacket may allow a thermal coupling medium to contact the chamber while also keeping the thermal coupling medium separate from an acoustic coupling medium. This arrangement may be useful, for example, where a particular type of material (such as water) is best used for acoustic coupling, while a different material (such as an antifreeze solution) is best used for thermal coupling.

In one illustrative embodiment, the chamber may have a barrel shape, and the inlet and outlet may each include a conduit that extends away from the chamber along a longitudinal axis of the barrel shape. Thus, the chamber may, in some sense, depend from the inlet and outlet or otherwise be positioned below the inlet and outlet conduits. The chamber may be used with a vessel that has an internal volume and an opening through which the chamber may be passed so as to be positioned in the vessel. The acoustic energy source may also be located in the vessel along with a coupling medium. A cap may be arranged to close the opening of the vessel, e.g., so as to enclose the chamber in the vessel. The inlet and outlet may each include a conduit that extends away from the chamber and passes through the cap so that material may be introduced into the chamber even though the vessel may be otherwise completely sealed from an external environment.

In another illustrative embodiment, the chamber may include an insert element that defines, at least in part, a shape and size of the internal volume. The insert element, which may include two or more separate parts or a single component, may be provided in the chamber to serve any one of several functions, such as providing a plurality of nucleation sites for cavitation, providing catalyst or other sites for enhancing reactions, defining the internal volume to have a particular shape, size or other configuration, helping to transfer heat into/out of the internal volume, and so on. For example, the insert element may define the internal volume to have a size and shape that closely matches or otherwise interacts with a focal zone of acoustic energy in the chamber. The insert element may be made of any suitable material, such as a ceramic material, may include components of any suitable size or shape, such as a plurality of rod members, or have other desired features.

In another aspect of the invention, a system for acoustically treating a material includes a chamber defining an internal volume and having an inlet to provide an inflow of material into the internal volume and an outlet to discharge an outflow of material from the internal volume. An acoustic energy source may be spaced from the chamber and arranged to emit acoustic energy having a frequency of about 100 kHz to 100 MHz to create a focal zone of acoustic energy in the internal volume, e.g., for treating material in the internal volume. A coupling medium, which may be liquid or solid, may be arranged to transmit acoustic energy from the acoustic energy source to the chamber. A reservoir may contain a material to be treated by acoustic energy in the chamber, and an agitator may be arranged to mix or otherwise move the material within the reservoir. A supply conduit fluidly connected between the reservoir and the inlet of the chamber may deliver material from the reservoir to the chamber, and a return conduit fluidly connected between the reservoir and the outlet of the chamber may return material to the reservoir. In some embodiments, a pump may be arranged to cause the material to flow through the supply and return conduits, and a second reservoir may be provided that optionally receives material from the return conduit. For example, the return conduit may include a three-way valve or other arrangement that allows material to be directed to the second reservoir rather than be returned to the first reservoir.

In another aspect of the invention, a system for acoustically treating a material includes a chamber defining an internal volume and having an inlet to provide an inflow of material into the internal volume and an outlet to discharge an outflow of material from the internal volume. An acoustic energy source may be spaced from the chamber and arranged to emit acoustic energy having a frequency of about 100 kHz to 100 MHz to create a focal zone of acoustic energy in the internal volume, e.g., to treat the material in the chamber. A coupling medium may be arranged to transmit acoustic energy from the acoustic energy source to the chamber. A first conduit may be fluidly connected to the inlet of the chamber, and a second conduit may be fluidly connected to the outlet of the chamber so that material in the conduits is caused to flow in a first direction from the first conduit through the internal volume and into the second conduit, and subsequently to flow in a second direction from the second conduit through the internal volume and into the first conduit. Flow of the material may be caused by a pump, gravity or other motive force, and the first and/or second conduits may be connected to a respective reservoir that serves to hold material as necessary.

In another aspect of the invention, a system for acoustically treating a material may include first and second acoustic treatment assemblies that are arranged in series. That is, material may be treated in a first chamber, and then delivered for subsequent treatment in a second chamber. Each of the treatment assemblies may include a chamber defining an internal volume and having an inlet to receive an inflow of material into the internal volume and an outlet to discharge an outflow of material from the internal volume, an acoustic energy source spaced from the chamber and arranged to emit acoustic energy having a frequency of about 100 kHz to 100 MHz to create a focal zone of acoustic energy in the internal volume, and a coupling medium arranged to transmit acoustic energy from the acoustic energy source to the chamber. A reservoir may be arranged to contain a material to be treated by acoustic energy in the chambers of the first and second acoustic treatment assemblies, and a supply conduit may be fluidly connected between the reservoir and the inlet of the first treatment assembly. A transfer conduit may be fluidly connected between the outlet of the first treatment assembly and the inlet of the second treatment assembly, e.g., to transfer material from the first chamber to the second chamber.

These and other aspects of the invention will be understood from the following description and claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

DETAILED DESCRIPTION

"Sonic energy" as used herein is intended to encompass such terms as acoustic energy, acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. "Focal zone" or "focal point" as used herein means an area where sonic energy converges and/or impinges on a target, although that area of convergence is not necessarily a single focused point, but may include a volume of varying size and shape. As used herein, the terms "process chamber" or "processing zone" as used herein means a vessel or region where the sonic energy converges, and the sample material is present for treatment. As used herein, "nonlinear acoustics" can mean lack of proportionality between input and output. For example, as the amplitude applied to the acoustic transducer increases, the sinusoidal output loses proportionality such that eventually the peak positive pressure increases at a higher rate than the peak negative pressure. Also, water becomes nonlinear at high acoustic energy intensities, and in a converging acoustic field, the waves become more disturbed as the intensity increases toward the focal point. Nonlinear acoustic properties of tissue can be useful in diagnostic and therapeutic applications. As used herein, "acoustic streaming" can mean generation of fluid flow by acoustic waves. The effect can be non-linear. Bulk fluid flow of a liquid in the direction of the sound field can be created as a result of momentum absorbed from the acoustic field. As used herein, "acoustic micro-streaming" can mean time-independent circulation that occurs only in a small region of the fluid around a source or obstacle, for example, an acoustically driven bubble in a sound field. As used herein, "acoustic absorption" can refer to a characteristic of a material relating to the material's ability to convert acoustic energy into thermal energy. As used herein, "acoustic impedance" can mean a ratio of sound pressure on a surface to sound flux through the surface, the ratio having a reactance and a resistance component. As used herein, "acoustic window" can mean a system or device for allowing sonic energy to pass through to the sample within the processing chamber or zone. As used herein, "acoustic lens" can mean a system or device for spreading, converging or otherwise directing sounds waves. As used herein, "acoustic scattering" can mean irregular and multi-directional reflection and diffraction of sound waves produced by multiple reflecting surfaces, the dimensions of which are small compared to the wavelength, or by certain discontinuities in the medium through which the wave is propagated.

Apparatus and Methods for Ultrasonic Treatment

Figure 1:
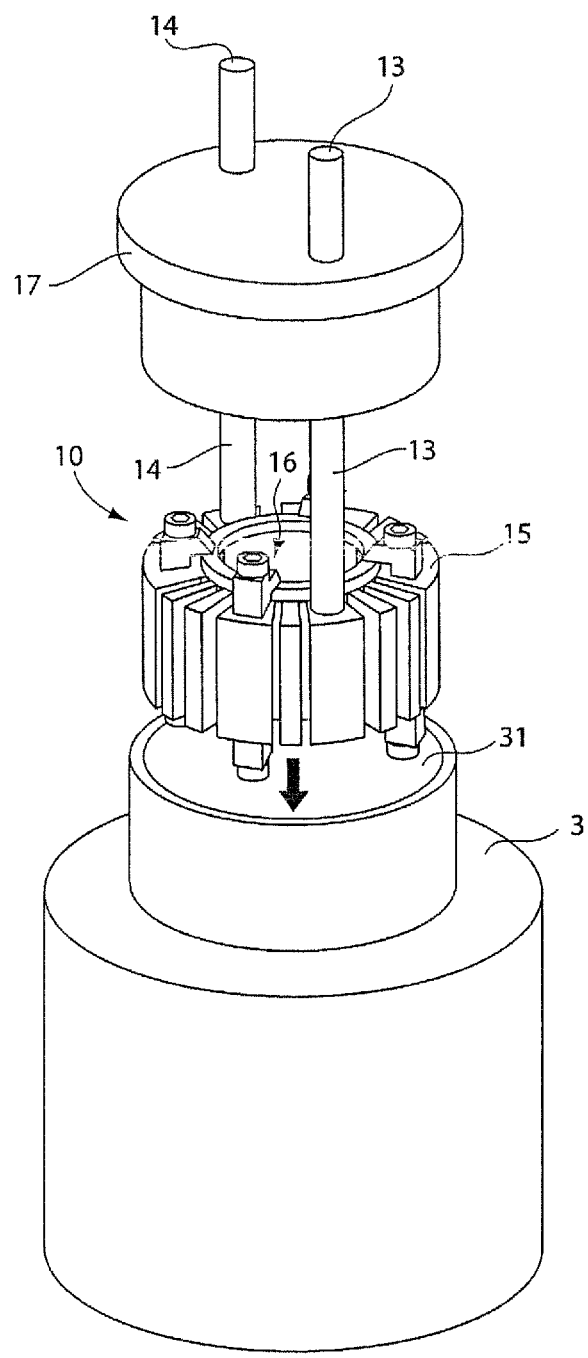
FIG. 1 is an exploded perspective view of an acoustic treatment system in an embodiment including a chamber that is received in a vessel.
Figure 2:
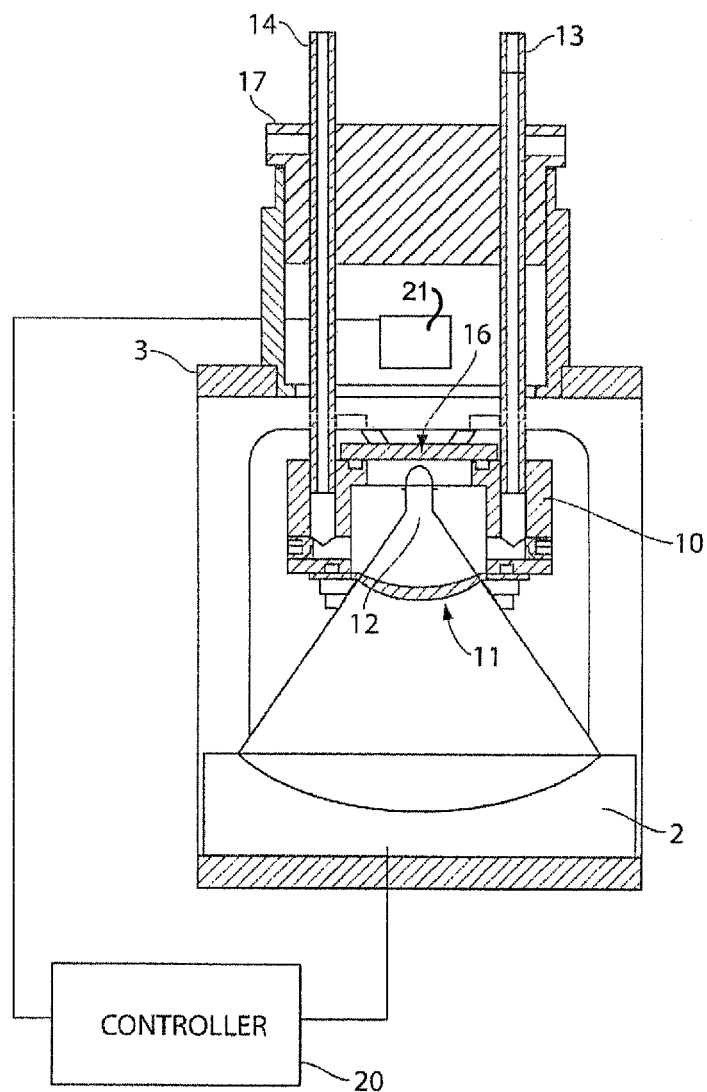
FIG. 2 is a cross sectional view of the FIG. 1 embodiment in an assembled condition.

FIGS. 1 and 2 depict one embodiment of a processing chamber 10, where focused acoustic energy generated by an acoustic energy source 2 passes through an acoustic window 11 of the chamber and into an internal volume 12 of the chamber 10 where the sample material is located. As is discussed in more detail below, the acoustic treatment system 1 may include a controller 20 (e.g., including a suitably programmed general purpose computer or other data processing device) that receives control information (e.g., from one or more sensors, user input devices, etc.) and correspondingly controls operation of the acoustic energy source 2 and/or other system components. Sample material is provided into the internal volume 12 via an inlet 13 and is removed from the volume 12 via an outlet 14. The inlet and outlet may be arranged in a variety of ways, and in this embodiment the inlet 13 and outlet 14 each include a conduit coupled to the chamber 10. In some embodiments, the inlet and/or outlet may include a check valve, one-way valve, electronically-controlled valves or other arrangement that helps to ensure that flow occurs in a desired way, e.g., so the flow of material is always from the inlet to the outlet even though flow may be intermittent. The internal volume 12 may be sized and shaped as appropriate for the material to be treated, e.g., some acoustic treatment applications (such as sterilization) may function more effectively if a relatively small volume of material is treated in a relatively small volume, whereas other applications (such as mixing) may produce better results using a larger volume for the internal volume 12. The internal volume 12 can have different shapes or other configuration characteristics, e.g., the internal volume 12 may be defined by vertical walls, can have a conical shape, can have a curved shape, and so on. Also, the chamber 10 can be made of multiple components such as an upper member, lower acoustically transparent member, and a body which together define the internal volume that contains the material to be treated. Alternately, the chamber 10 may be made as a single unitary piece or in other ways.

Figure 3:
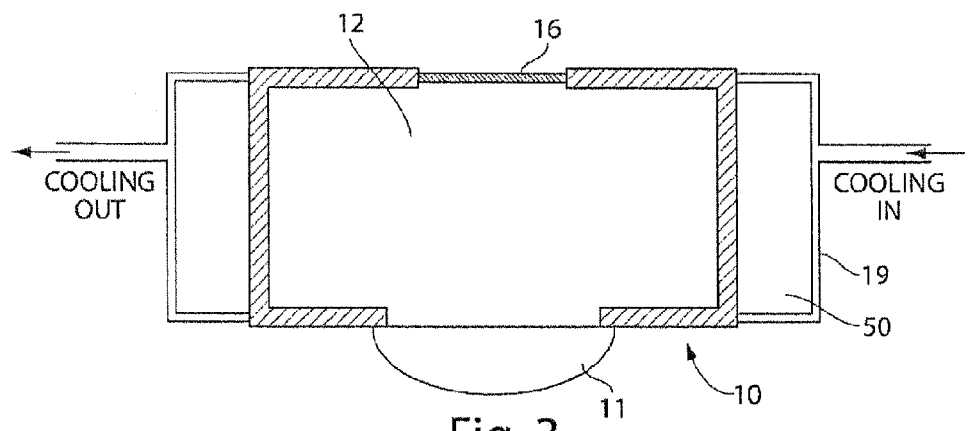
FIG. 3 is a cross sectional view of an acoustic treatment chamber having a jacketed heat exchanging system.

One or more walls of the chamber 10 may serve as, or otherwise be associated with, a thermal transfer mechanism, or heat exchanger, to dissipate any heat generated in the internal volume 12 and/or to receive heat from outside of the chamber 10 that is transferred into the internal volume 12. As can be seen in FIG. 1, the chamber 10 may include a heat exchanger 15 in the form of a plurality of radial fins. Of course, the heat exchanger 15 could be formed in other ways, such as including a Peltier device that uses electrical power to transfer heat from one location to another, an electric resistance heater, heat conducting rods, tubes or other structures, phase-changing materials used to transfer heat from one location to another, and so on. The heat exchanger 15 may be arranged to operate with any suitable thermal coupling medium, such as air or other gas, water or other liquid, or a solid material. For example, as shown in FIG. 2, the chamber 10 may be completely or partially submerged in a liquid that serves to transmit heat with respect to the heat exchanger 15. Close thermal coupling between water or other outside thermal coupling medium and the internal volume 12 may help control of the temperature of the material in the internal volume 12 during acoustic processing. Control of the temperature of the coupling medium 4 can help control temperature in the internal volume 12. For example, the coupling medium 4 can be recirculated through a chiller, a heater, or other means to adjust the temperature of the coupling medium 4. Thus, the sample material inside the chamber 10 can be thermally linked to the coupling medium 4 temperature by careful consideration of the design of the chamber 10. The thermal coupling between the inside wall of the chamber 10 and the sample material may be tightly linked, due to high mixing, turbulence, and activity/or at the surface of the internal wall, thus creating high convective heat transfer. Heat can pass either through one or more ends of the chamber 10 (e.g., at the windows 11 and 16), or through the side walls of the vessel before being linked to the coupling medium 4 bulk temperature. Note that heat can flow in either direction, depending on the relative difference between the coupling medium and the sample material temperature, and the desired target of maintaining the sample at a target temperature to achieve the desired effect. The transfer between the chamber 10 internal wall and the coupling medium can be achieved by simple conduction through the wall to the outside surface, or the external surface area can be enhanced through the use of fins or other high heat transfer effects such as a jacketed vessel with pumped fluid. For example, FIG. 3 shows an illustrative arrangement in which a jacket 19 is positioned around at least part of the chamber 10 and a thermal transfer medium 50 is circulated in the space between the jacket 19 and the chamber 10 external wall. In addition, the inlet and/or outlet conduits can also be coupled to the coupling medium temperature and/or the thermal transfer medium by the use of enhanced thermal surfaces at the inlet, or outlet of the chamber 10. For example, although not shown in FIG. 3, the inlet 13 and/or outlet 14 may pass through the space between the jacket 19 and the chamber 10 so as to transfer heat with respect to the thermal transfer medium 50. Alternately, the inlet and/or outlet medium conduit may include heat exchanger features that allow heat to be transferred with respect to the acoustic coupling medium 4.

In certain embodiments, the acoustic energy source 2 may include an ultrasound transducer that projects a focused ultrasound beam or wave front toward the window 11 of the chamber 10. The window 11, which may sealingly close an opening in the chamber 10, may be suitably transparent to, or otherwise transmit acoustic energy so that the ultrasound beam penetrates the window 11 to form a focal zone within the internal volume 12 that acts upon the material in the chamber 10. The window 11 may be configured to transmit a maximum amount of ultrasound energy to the material in the chamber 10, minimize the absorption of ultrasound energy within the walls of the chamber 10, and/or maximize heat transfer between the internal volume 12 and, for example, an external water bath or other coupling medium. In certain embodiments, the window 11 is glass, sapphire, quartz or a polymer such as a thin film polymer. The window may have any suitable shape or other configuration, e.g., may be flat (or otherwise present a relatively flat surface to the impinging acoustic energy), or may be curved so as have a hemispherical or other convex shape. In certain embodiments, the window 11 is shaped to guide the sonic energy in a preferred manner relative to the internal volume 12, such as focusing or defocusing the acoustic energy, through a 'lense' effect caused by the physical shape of the window 11 (such as an effect caused by a concave or convex shape). In some embodiments, the window 11 has an acoustic impedance similar to that of water and a relatively low acoustic absorption. One preferred material is low density polyethylene, but other polymers such as polypropylene, polystyrene, poly(ethylene teraphthalte) ("PET"), polyimide, and other rigid and flexible polymers may be used. If the window 11 is formed from a thin film material, the film may be a laminate to facilitate thermal bonding to the chamber 10. For example, the window 11 may be sealingly attached to the chamber 10 using heat sealing. Thicker, more rigid materials may also be employed for the window 11.

The upper portion of the chamber 10 may include an inspection window 16, which can be flat or domed or otherwise arranged to enclose the internal volume 12 while permitting visible light inspection of the internal volume 12. Such inspection may be done by a human, or by a suitably arranged sensor 21 such as a video camera, photodetector, IR detector, and so on. Characteristics of the material in the internal volume 12 detected by the sensor 21 may be used by the controller 20 to control the acoustic energy source 2 or other components of the system 1. For example, if excessive cavitation is to be avoided, the controller 20 may adjust the acoustic energy at the focal zone if the sensor 21 detects the presence of cavitation bubbles of a certain size and/or number. Other features may be detected by the sensor 21, such as the size, density or other characteristics of particles in the chamber 10 in the case where the acoustic treatment is intended to break down the size of particles in the sample material. Thus, the sensor 21 may detect whether acoustic treatment is progressing as desired and whether processing is complete, e.g., to trigger the introduction of additional sample material into the chamber 10. Like the window 11, the inspection window 16 may be formed of any suitable material, such as glass, sapphire, quartz, and/or polymer materials.

The body of the chamber 10 may be made of any material or combination of materials suitable to contain the material in the internal volume 12 during treatment, to act as an environmental seal, and/or to provide a thermal transfer mechanism. In some embodiments, the chamber 10 may be made of a rigid or flexible material, such as a thermally conductive metal or polymer, or a combination of such materials. Preferably, the material used for the chamber 10 has a low acoustic absorption and acceptable heat transfer properties for a desired application. In certain embodiments, the upper portion of the chamber 10 (e.g., including the inspection window 16) can be arranged to reflect acoustic energy back into the internal volume 12, providing additional process efficiencies. If the chamber 10 is made from multiple parts, such as by upper and lower members, the members may be joined together by thermal bonding, adhesive bonding, external clamping, mechanical fasteners (such as the bolts shown in FIG. 1) with an o-ring or other gasket to form a seal between the members, welding, and so on. If the bond is to be achieved by thermal bonding, the upper and lower members may be made of, or include, film laminates having heat bondable outer layers and heat resistant inner layers.

As can be seen in FIG. 2, the acoustic treatment system 1 may include a vessel 3 that contains the acoustic energy source 2, the chamber 10 as well as a coupling medium 4. The vessel 3 may take any suitable size, shape or other configuration, and may be made of any suitable material or combination of materials (such as metal, plastic, composites, etc.). In this illustrative embodiment, the vessel 3 has a jar- or can-like configuration with an opening 31 arranged to permit access to an internal volume of the vessel 3. The acoustic energy source 2 and the coupling medium 4 (such as water or other liquid, or optionally a solid material) may be positioned in the vessel 3, e.g., with the acoustic energy source 2 near a bottom of the vessel 3. (If the coupling material 4 is solid, the vessel 3 and the coupling medium 4 may be essentially integrated with each other, with the coupling medium 4 essentially functioning as an acoustic coupling as well as a physical attachment of the acoustic source 2 and the chamber 10.) The opening 31 may be arranged so that the chamber 10 can be lowered into the vessel 3, e.g., so that the chamber 10 is partially or completely submerged in the coupling medium 4. The coupling medium 4 may function as both an acoustic coupling medium, e.g., to transmit acoustic energy from the acoustic energy source 2 to the window 11, as well as a thermal coupling medium, e.g., to accept heat energy from the chamber 10. In other embodiments, the thermal and acoustic coupling medium may be separate, e.g., where the chamber 10 is provided with a cooling jacket 19 like that in FIG. 3.

In this illustrative embodiment, the opening 31 is sized and shaped to receive the chamber 10, which has a barrel shape in this embodiment with the inlet 13 and outlet 14 extending generally along the longitudinal axis of the barrel shape of the chamber 10. A cap 17 is engaged with the inlet 13 and outlet 14 conduits and is arranged so that the chamber 10 may be suspended in the coupling medium 4, supported by the inlet and outlet conduits and the cap 17. The chamber 10 may be positioned in the vessel 3 so that a focal zone of acoustic energy created by the acoustic energy source 2 is suitably located in the internal volume 12 of the chamber 10. Thus, assembly of the system 1 may be eased because appropriate positioning of the chamber 10 relative to the acoustic energy source 2 may be achieved by simply engaging the cap 17 with the opening 31 of the vessel 3. No adjustment of the chamber 10 position in the vessel 3 need be required as long as the chamber is suitably positioned relative to the cap 17 and the cap 17 is properly engaged with the vessel 3. The cap 17 may engage with the opening 31 of the vessel 3 so that not only the cap 17/chamber 10 are supported by the vessel 3, but also so that the vessel opening 31 is sealed or otherwise closed by the cap 17, e.g., to help prevent contamination of the coupling medium 4. The inlet and outlet conduits may pass through the cap 17, e.g., for fluid connection to supply and/or return lines or other conduits that carry the material to be treated in the chamber 10.

It should be understood that the chamber 10 may be arranged in any suitable way, and for a variety of different applications. For example, in the embodiment shown in FIG. 2, the inlet 13 and outlet 14 communicate with the internal volume 12 on opposite sides of the volume 12 and at a same vertical level. However, the inlet 13 and outlet 14 may communicate with the internal volume 12 in other ways, e.g., the inlet 13 may be fluidly coupled with the internal volume 12 at a location that is above, or below, of a location where the outlet is fluidly coupled to the internal volume. Having the inlet and outlet coupled at different heights may provide advantages depending on the specific application. For example, in some applications, having the inlet located above the outlet may help control the temperature of the material in the internal volume 12, e.g., cooler fluid entering at the inlet may mix with relatively warm fluid near a top of the internal volume 12. In other applications, having the inlet below the outlet may help ensure that material having a desired size or density is encouraged to exit at the outlet, e.g., larger, more dense particles may remain in the internal volume 12 below the outlet until the particles are broken down by the acoustic treatment into a desired size/density range. In the case of a water jacketed chamber, positioning the inlet and outlet at opposite ends of the chamber can enable counter-flow heat exchanger operation and improved heat transfer and temperature control of the sample.

Figure 4:
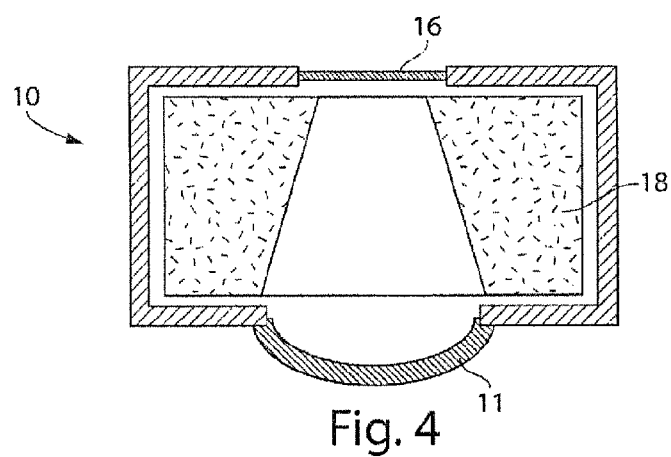
FIG. 4 is a cross sectional view of an acoustic treatment chamber having an insert element in one illustrative embodiment.
Figure 5:
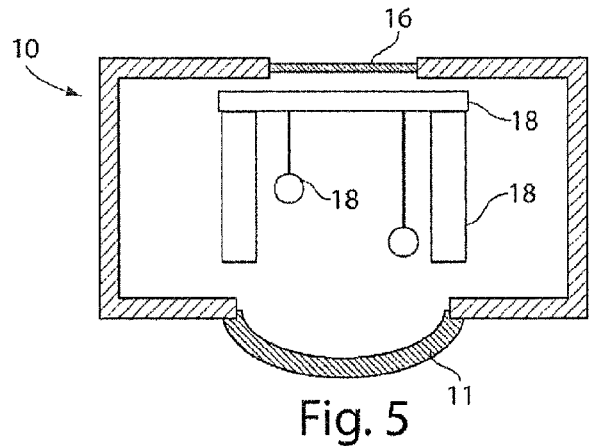
FIG. 5 is a cross sectional view of an acoustic treatment chamber having an insert element that includes suspended rods and spherical elements in an illustrative embodiment.

In accordance with another aspect of the invention, the chamber 10 may include one or more insert elements that may be provided in the internal volume 12 to define, at least in part, a shape and size of the internal volume. For example, as shown in FIG. 4, an insert element 18 having a sleeve arrangement with an outer cylindrical shape and an inner conical or frustoconical shape may be provided in the internal volume 12 to define the size and shape of the internal volume 12 where acoustic treatment will take place. In this embodiment, the inner space defined by the insert element 18 functions as the internal volume 12 where material is acoustically treated. The insert element 18 may be made in a variety of different shapes, sizes and materials, depending on the application or other desired function. For example, the insert element 18 may include a plurality of nucleation sites, e.g., provided by the surface of a ceramic material of the insert element 18, that serve as initiation sites for cavitation. Other arrangements are possible, including ceramic rods, beads or elements made of other materials, that are positioned in the internal volume 12 and function to provide nucleation sites, to help transfer or otherwise distribute heat in the chamber 10, provide reaction sites or otherwise catalyze or aid in chemical or other reactions in the volume 12, and other functions. The rods, beads or other structures may be suspended in the internal volume 12, e.g., as shown in FIG. 5 by a physical support and/or by mixing or other fluid movement in the internal volume caused by the acoustic energy or other material flow.

In accordance with an aspect of the invention, the system 1, e.g., as shown in FIGS. 1 and 2 as well as other embodiments described below, may be arranged to accommodate continuous acoustic treatment of material in a chamber 10, or multiple chambers 10, for an extended time period, e.g., for 1 hour or more, at a relatively high intensity, e.g., at an output of the acoustic transducer of 200 watts or more, without experiencing excessive heat buildup or other problems. In one embodiment, a piezoelectric transducer functioning at part of the acoustic energy source 2 may operate at an intensity level equal to about 286 watts for several hours in an equilibrium state, i.e., a state in which material is acoustically processed in a chamber 10 without excessive heat build up, transducer burn out or failure, or other conditions that would require stoppage of the acoustic treatment. This is in contrast to prior acoustic treatment arrangements in which continuous acoustic treatment for 1 hour or more could not have been achieved for a variety of different reasons, such as excessive heat buildup, failure of the acoustic source (e.g., due to transducer overheating and subsequent burn out), damage to the sample material, and so on.

Transducer

In certain embodiments, the sonic energy source 2 may include, for example, an ultrasound transducer or other transducer, that produces acoustic waves in the "ultrasonic" frequency range. Ultrasonic waves start at frequencies above those that are audible, typically about 20,000 Hz or 20 kHz, and continue into the region of megahertz (MHz) waves. The speed of sound in water is about 1000 meters per second, and hence the wavelength of a 1000 Hz wave in water is about a meter, typically too long for specific focusing on individual areas less than one centimeter in diameter, although usable in non-focused field situations. At 20 kHz the wavelength is about 5 cm, which is effective in relatively small treatment vessels. Depending on the sample and vessel volume, preferred frequencies may be higher, for example, about 100 kHz, about 1 MHz, or about 10 MHz, with wavelengths, respectively, of approximately 1.0, 0.1, and 0.01 cm. In contrast, for conventional sonication, including sonic welding, frequencies are typically approximately in the tens of kHz, and for imaging, frequencies are more typically about 1 MHz and up to about 20 MHz. In lithotripsy, repetition rates of pulses are fairly slow, being measured in the hertz range, but the sharpness of the pulses generated give an effective pulse wavelength, or in this case, pulse rise time, with frequency content up to about 100 to about 300 MHz, or 0.1-0.3 gigahertz (GHz).

The frequency used in certain embodiments of the invention also will be influenced by the energy absorption characteristics of the sample or of the chamber 10, for a particular frequency. To the extent that a particular frequency is better absorbed or preferentially absorbed by the sample material, it may be preferred. The energy can be delivered in the form of short pulses or as a continuous field for a defined length of time. The pulses can be bundled or regularly spaced.

A generally vertically oriented focused ultrasound beam may be generated in several ways by the acoustic energy source 2. For example, a single-element piezoelectric transducer, such as those supplied by Sonic Concepts, Woodinville, Wash., that can be a 1.1 MHz focused single-element transducer, can have a spherical or other curved transmitting surface that is oriented such that the focal axis is vertical. Another embodiment uses a flat unfocused transducer and an acoustic lens (e.g., the window 11 or other element) to focus the beam. Still another embodiment uses a multi-element transducer such as an annular array in conjunction with focusing electronics to create the focused beam. The annular array potentially can reduce acoustic sidelobes near the focal point by means of electronic apodizing, that is by reducing the acoustic energy intensity, either electronically or mechanically, at the periphery of the transducer. This result can be achieved mechanically by partially blocking the sound around the edges of a transducer or by reducing the power to the outside elements of a multi-element transducer. This reduces sidelobes near the energy focus, and can be useful to reduce heating of the chamber 10. Alternatively, an array of small transducers can be synchronized to create a converging beam. Still another embodiment combines an unfocused transducer with a focusing acoustic mirror to create the focused beam. This embodiment can be advantageous at lower frequencies when the wavelengths are large relative to the size of the transducer. The axis of the transducer of this embodiment can be horizontal and a shaped acoustic mirror used to reflect the acoustic energy vertically and focus the energy into a converging beam.

In certain embodiments, the focal zone can be small relative to the dimensions of the treatment chamber 10 to avoid heating of the treatment chamber 10. In one embodiment, the focal zone has a width of approximately 1 mm. Heating of the treatment chamber 10 can be reduced by minimizing acoustic sidelobes near the focal zone. Sidelobes are regions of high acoustic intensity around the focal point formed by constructive interference of consecutive wavefronts. The sidelobes can be reduced by apodizing the transducer either electronically, by operating the outer elements of a multi-element transducer at a lower power, or mechanically, by partially blocking the acoustic waves around the periphery of a single element transducer. Sidelobes may also be reduced by using short bursts, for example in the range of about 3 to about 5 cycles in the treatment protocol.

The transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing. The response is linear if not overdriven. The high-energy focus zone of one of these domes is typically cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as having an acoustic intensity within about 6 dB of the peak acoustic intensity, is formed around the geometric focal point.

The wavelength, or characteristic rise time multiplied by sound velocity for a shock wave, is in the same general size range as a biological cell, for example about 10 to about 40 micron. This effective wavelength can be varied by selection of the pulse time and amplitude, by the degree of focusing maintained through the interfaces between the source and the material to be treated, and the like.

Another source of focused acoustic pressure waves is an electromagnetic transducer and a parabolic concentrator, as is used in lithotripsy. The excitation of such devices tends to be more energetic, with similar or larger focal regions. Strong focal peak negative pressures of about −16 MPa have been observed. Peak negative pressures of this magnitude provide a source of cavitation bubbles in water, which can be desirable in an extraction process.

Drive Electronics and Waveform Control.

One treatment protocol for treating material with acoustic energy in the chamber 10 can include variable acoustic waveforms combined with sample motion and positioning to achieve a desired effect. The acoustic waveform of the transducer may have many effects, including: acoustic microstreaming in and near cells due to cavitation, that is flow induced by, for example, collapse of cavitation bubbles; shock waves due to nonlinear characteristics of the fluid bath; shock waves due to cavitation bubbles; thermal effects, which lead to heating of the sample, heating of the sample vessel, and/or convective heat transfer due to acoustic streaming; flow effects, causing deflection of sample material from the focal zone due to shear and acoustic pressure, as well as mixing due to acoustic streaming, that is flow induced by acoustic pressure; and chemical effects. The waveform of focused sound waves can be a single shock wave pulse, a series of individual shock wave pulses, a series of shock wave bursts of several cycles each, or a continuous waveform. Incident waveforms can be focused directly by either a single element, such as a focused ceramic piezoelectric ultrasonic transducer, or by an array of elements with their paths converging to a focus. Alternatively, multiple foci can be produced to provide ultrasonic treatment to multiple treatment zones, vessels, or wells. Additionally, the flow of the sample material into, or out of the processing chamber 10 can interact with the acoustic effects, and the acoustic streaming can be modified to enhance this sample flow in a desirable manner.

The treatment protocol can be optimized to maximize energy transfer while minimizing thermal and flow effects. The treatment protocol also can effectively mix the contents of the treatment chamber 10, in the case of a particulate sample suspended in a liquid. Energy transfer into the sample can be controlled by adjusting the parameters of the acoustic wave such as frequency, amplitude, and cycles per burst. Temperature rise in the sample can be controlled by limiting the duty cycle of the treatment and by optimizing heat transfer between the treatment chamber 10 and the coupling medium 4. Heat transfer can be enhanced by making the treatment chamber 10 with thin walls, of a relatively highly thermally conductive material, and/or by promoting forced convection by acoustic streaming in the treatment chamber 10 and in the fluid bath in the proximity of the treatment chamber 10. Additionally, the chamber 10 can be modified to enhance the thermal coupling between the sample and the exterior environment by providing enhanced surface treatments such as increased area such as fins, an actively pumped water jacket, and/or high conductivity vessel materials. Monitoring and control of temperature is discussed in more detail below.

For example, for a cellular disruption and extraction treatment, an example of an effective energy waveform is a high amplitude sine wave of about 1000 cycles followed by a dead time of about 9000 cycles, which is about a 10% duty cycle, at a frequency of about 1.1 MHz. The sine wave electrical input to the transducer typically results in a sine wave acoustic output from the transducer. As the focused sine waves converge at the focal point, they can become a series of shock waves due to the nonlinear acoustic properties of the water or other fluid in the coupling medium 4. This protocol treats the material in the focal zone effectively during the "on" time. As the material is treated, it is expelled from the focal zone and new material circulates into the focal zone. The acoustic "on" and "off" times can be cycled to be effective, for example, for extracting the cellular contents of ground or particulate leaf tissue, while causing minimal temperature rise in the treatment vessel.

Further advantage in disruption and other processes may be gained by creating a high power "treat" interval alternating with a low power "mix" interval. More particularly, in this example, the "treat" interval utilizes a sine wave that has a treatment frequency, a treatment cycles-per-burst count, and a treatment peak-to-peak amplitude. The "mix" interval has a mix frequency, a mix cycles-per-burst count and a lower mix peak-to-peak amplitude. Following each of the intervals is a dead time. Of course, these relationships are merely one example of many, where one interval in considered to be high power and one interval is considered to be low power, and these variables and others can be altered to produce more or less energetic situations. Additionally, the treat function or interval and the mix function or interval could emit from different or multiple transducers in the same apparatus, optionally emitting at different frequencies.

High power/low power interval treatments can allow multiple operations to be performed, such as altering permeability of components, such as cells, within the sample followed by subsequent mixing of the sample. The treat interval can maximize cavitation and bioeffects, while the mix interval can maximize mixing within the treatment vessel and/or generate minimal heat. Adding a longer, high power "super-mix" interval occasionally to stir up particles that are trapped around the periphery of the chamber 10 can provide further benefits. This "super-mix" interval generates additional heat, so it is programmed to treat infrequently during the process, for example, every few seconds. Additionally, dead times between the mix and treat intervals, during which time substantially no energy is emitted from the sonic energy source, can allow fresh material to circulate into the energy focal zone of the target.

The waveform of the sound wave typically is selected for the particular material being treated. For example, to enhance cavitation, it can be desirable to increase the peak negative pressure following the peak positive pressure. For other applications, it can be desirable to reduce cavitation, but maintain the peak positive pressure. This result can be achieved by performing the process in a pressurized chamber 10 at a slight pressure above ambient. For example, if the waveform generated has a peak negative pressure of about −5 MPa, then the entire chamber may be pressurized to about 10 MPa to eliminate cavitation from occurring during the process. Material to be treated can be pressurized on a batch or a continuous basis within the internal volume 12 of the chamber 10. That is, a volume of material may be delivered into the internal volume 12, treated acoustically while material flow is stopped, and then a new volume of material may be delivered into the internal volume 12 once treatment of the initial volume is complete.

Typically, the shock wave is characterized by a rapid shock front with a positive peak pressure in the range of about 15 MPa, and a negative peak pressure in the range of about negative 5 MPa. This waveform is of about a few microseconds duration, such as about 5 microseconds. If the negative peak is greater than about 1 MPa, cavitation bubbles may form. Cavitation bubble formation also is dependent upon the surrounding medium. For example, glycerol is a cavitation inhibitive medium, whereas liquid water is a cavitation promotive medium. The collapse of cavitation bubbles forms "microjets" and turbulence that impinge on the surrounding material.

Control of the acoustic energy source 2 may be performed by the controller 20 using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system 1. A variety of sensors or sensed properties may be used by the controller 20 for providing input for feedback control. These properties can include sensing of temperature of the sample material; sonic beam intensity; pressure; coupling medium properties including temperature, salinity, and polarity; sample material position; conductivity, impedance, inductance, and/or the magnetic equivalents of these properties, and optical or visual properties of the sample material. These optical properties, which may be detected by the sensor 21 typically in the visible, IR, and UV ranges, may include apparent color, emission, absorption, fluorescence, phosphorescence, scattering, particle size, laser/Doppler fluid and particle velocities, and effective viscosity. Sample integrity or comminution can be sensed with a pattern analysis of an optical signal from the sensor 21. Particle size, solubility level, physical uniformity and the form of particles could all be measured using instrumentation either fully stand alone sampling of the fluid and providing a feedback signal, or integrated directly with the focused acoustical system via measurement interface points such as an optical window. Any sensed property or combination thereof can serve as input into a control system. The feedback can be used to control any output of the system, for example beam properties, sample position or flow in the chamber 10, treatment duration, and losses of energy at boundaries and in transit via reflection, dispersion, diffraction, absorption, dephasing and detuning.

According to certain embodiments of the present invention, several aspects of the treatment system 1 can enhance the reproducibility and/or effectiveness of particular treatments using ultrasonic energy in in vitro applications, where reproducibility, uniformity, and precise control are desired. These aspects include the use of feedback, precise focusing of the ultrasonic energy, monitoring and regulating of the acoustic waveform (including frequency, amplitude, duty cycle, and cycles per burst), positioning of the chamber 10 relative to the ultrasonic energy so that the sample material is uniformly treated, controlling movement or flow of the sample relative to the focus of ultrasonic energy during a processing step, and/or controlling the temperature of the sample being treated, either by the ultrasonic energy parameters or through the use of temperature control devices such as a water bath. A treatment protocol can be optimized, using one or a combination of the above variables, to maximize, for example, shearing, extraction, permeabilization, comminution, stirring, or other process steps, while minimizing undesirable thermal effects.

In one embodiment of the invention, high intensity ultrasonic energy is focused on a chamber 10, and "real time" feedback relating to one or more process variables is used to control the process. In another embodiment, the process is automated and is used in a high throughput system, such as a continuous flowing stream of material to be treated, optionally segmented.

In certain embodiments, the processing system can include a high intensity transducer that produces acoustic energy when driven by an electrical or optical energy input; a device or system for controlling excitation of the transducer, such as an arbitrary waveform generator, an RF amplifier, and a matching network for controlling parameters such as time, intensity, and duty cycle of the ultrasonic energy; a system or method for transferring material into and out of the process zone, either actively or passively, to allow automation and the implementation of feedback from monitoring; a temperature sensor; a device for controlling temperature; one or more reaction chambers 10; and a sensor for detecting, for example, optical, radiative, and/or acoustic signatures. The feedback signal can also come from a signal provided by either external or integrated measurement methods such as particle size, solubility, and form factors.

Additional aspects of the invention relate to material flow circuit arrangements for acoustically treating the material. For example, in some embodiments the sample material can be transferred to/from the treatment chamber through passive or active means, with the use of direct pumping methods or passive gravity driven methods.

In one illustrative embodiment shown schematically in FIG. 4, an acoustic treatment system 1 may include one or more treatment chambers 10 that is fluidly coupled to a reservoir 30 that holds material to be treated in the chamber 10. In this illustrative embodiment, the inlet 13 of the chamber 10 is fluidly coupled to a supply conduit 31 and the outlet 14 of the chamber 10 is fluidly coupled to a return conduit 32. Thus, material in the reservoir 30 may be circulated through the chamber 10 at any suitable flow rate, pressure, time or other parameter so that the material is suitably processed by acoustic energy in the chamber 10. Flow of the material may be caused by gravity, by acoustic streaming (e.g., in the chamber 10), by a pump 33 (such as a syringe pump, a peristaltic pump, a gear pump, and so on), or other motive force. In some embodiments, a pressure may be maintained in the chamber 10 (and/or in the reservoir 30) by applying a pressurized gas, a pump or other component to generate the desired pressure in the desired locations. As discussed above, pressurizing the material in the chamber 10 and/or elsewhere may help reduce cavitation, enhance reaction rates, and/or have other desired affects.

Figure 6:
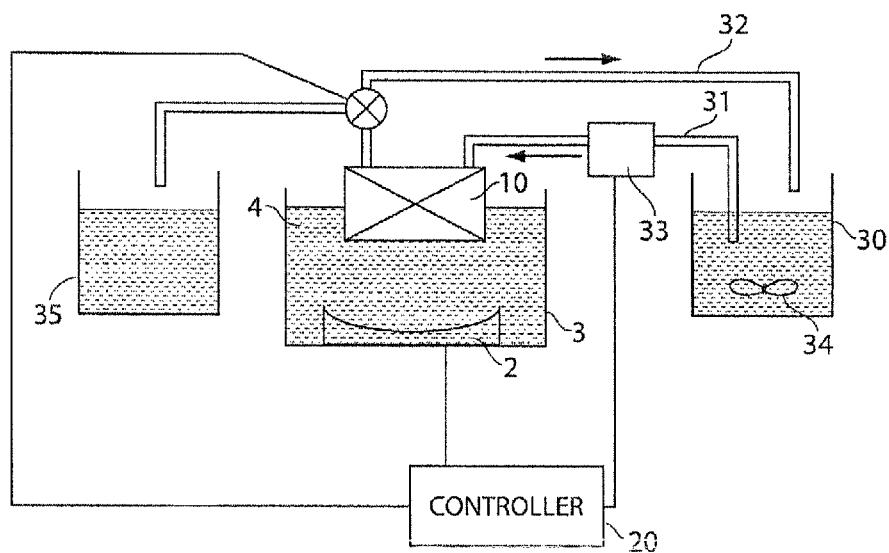
FIG. 6 is an illustrative embodiment of an acoustic treatment system including a reservoir with an agitator.

In one aspect of the invention, the reservoir 30 may include an agitator 34, such as a mixing blade, stirrer, homogenizer or other device that functions to mechanically mix, shear or otherwise cause movement of the material in the reservoir 30. Movement of the material may have desired affects, such as pretreating the material prior to acoustic treatment, maintaining a desired distribution of material components throughout the volume in the reservoir, and so on. An arrangement like that in FIG. 6 may allow the system 1 to repeatedly expose the material to acoustic treatment so that the material has desired properties when treatment is complete. The acoustic treatment conditions in the chamber 10 may remain constant, or nearly constant throughout the process, or the conditions may change over time. For example, the material may initially include relatively large particles of a substance to be broken down into smaller particles and ultimately solublized in a carrier liquid. Initial acoustic treatment conditions (as well as operation of the agitator 34) may be favorable to break the large particles down into smaller particles. After some initial treatment, the large particles may be broken down, and the acoustic treatment conditions (and the operation of the agitator 34) may be adjusted to enhance the speed and effectiveness of putting components of the small particles into solution. Adjustments to the treatment conditions may be made based on any suitable criteria, such as sensed material properties (such as particle size, density, etc.), a time elapsed, user input, and so on. The system 1 may optionally include a second reservoir 35 that receives material when processing of the material is determined to be complete (again, which determination may be made based on detected material properties, elapsed time, etc.). In this embodiment, the return conduit 32 includes a three-way valve 36 (or other suitable arrangement) that permits the controller 20 to direct material to the second reservoir 35 as desired. Of course, other flow control arrangements may be used, and control of material flow to the second reservoir 35 may be based on sensed parameters, such as elapsed processing time, detected particle sizes or density, material color or other optical properties, or other characteristics of the sample material.

Figure 7:
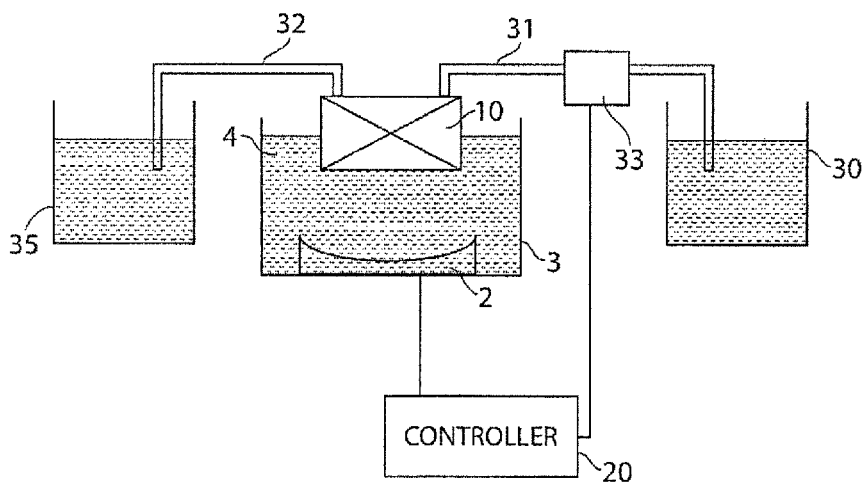
FIG. 7 is an illustrative embodiment of an acoustic treatment system arranged for oscillating flow of material.

FIG. 7 shows another illustrative embodiment for an acoustic treatment system 1 that includes a first reservoir 30 fluidly coupled to a chamber 10 via a supply conduit 31, and a second reservoir 35 fluidly coupled to the chamber 10 via a return conduit 32. In this embodiment, material in the first reservoir 30 may flow through the chamber 10 for acoustic treatment, and thereafter be deposited in the second reservoir 35. In the case that subsequent acoustic treatment is desired, the material may be again caused to flow through the chamber 10, albeit in the opposite direction and into the first reservoir 30 after a second treatment. Flow of the material may be caused in any suitable way, such as by a pump 33, by acoustic streaming in the chamber 10, by gravity (e.g., by establishing the level of material in one reservoir to be higher than the other, causing a siphon to be created for flow), or others. The chamber 10 and/or the conduits 31, 32 may include one or more window, sensors or other components suitable to detect properties of the sample material. These detected features may be used to control various parameters of the system 1, such as flow rate, pressure, acoustic treatment characteristics, and so on.

Figure 8:
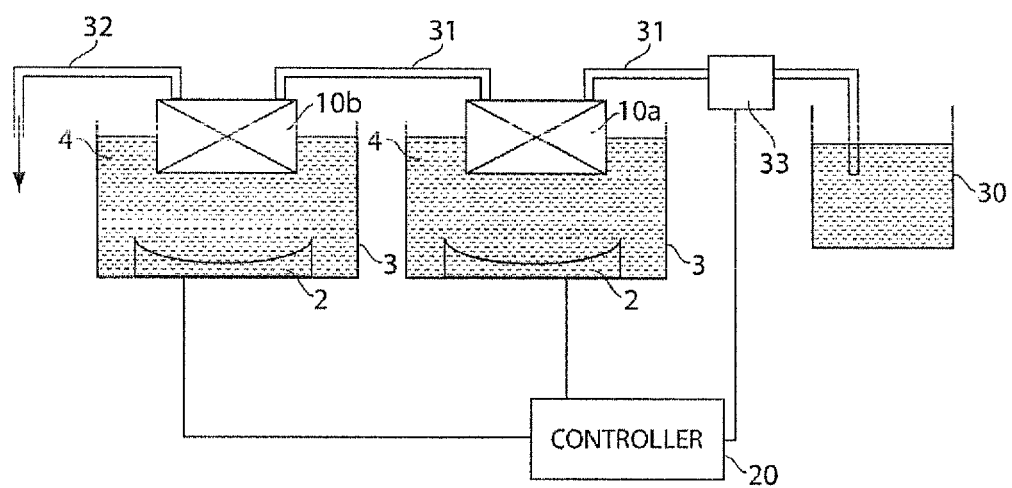
FIG. 8 is an illustrative embodiment of an acoustic treatment system arranged for serial treatment of material using multiple treatment chambers.

In another illustrative embodiment, an acoustic treatment system 1 may include two or more treatment chambers 10 that are arranged in serial fashion. For example, FIG. 8 shows an embodiment in which two chambers 10 are in fluid communication with each other and a reservoir 30. The first chamber 10a may be used to apply a 'pretreatment' or other first treatment to the sample material, while the second chamber 10b applies a 'finishing" or other second treatment to the material. The acoustic energy and other treatment parameters may be set and controlled independently at each chamber 10 to optimize the overall processing goals. For example, the sample material can first pass through a 'roughing' stage in the first chamber 10a to break up large chunks/clumping in the sample material (e.g., where the treatment conditions provide a general, high level mixing and homogenization of the sample) before the material passes to the next stage (e.g., a 'finishing' stage) for additional acoustic treatment that refines the ultimate properties of the material, such as by extracting desired materials, solubilizing components in the material, and so on. As many stages, i.e., chambers 10, as is necessary may be used in a system 1 like that in FIG. 8 to achieve the desired output.

Aspects of the invention also relate to methods for acoustically treating material using the various systems 1 described above. For example, one method in accordance with the invention involves treating a material using a system like that in FIG. 6 wherein material is agitated by an agitator in a reservoir, the material is caused to flow from the reservoir into a chamber 10, the material is exposed to focused acoustic energy in the internal volume of the chamber 10 (where the acoustic energy at a focal zone has the properties described herein), and the material is caused to flow back to the reservoir. Optionally, a processing state of the material may be detected, e.g., while the material is in the chamber 10 or return conduit, and if the material is suitably processed, the material may be caused to flow to an other reservoir. Relatively large volumes of material, such as 1 gallon, 10 gallons, 100 gallons, 1000 gallons or more of material may be held in the reservoir and caused to flow in a circulatory manner through one or more chambers 10 in a continuous fashion. Thus, the treatment method may be continuously performed for 1 hour or more, with the acoustic energy source continuously operating at a power output equivalent to 200 watts or more.

Another method in accordance with the invention relates to treating material using a system like that in FIG. 7 or a similar system. For example, material may be caused to flow in a first direction into a chamber 10, the material is exposed to focused acoustic energy in the internal volume of the chamber 10 (where the acoustic energy at a focal zone has the properties described herein), and the material is caused to flow out of the chamber 10. Thereafter, the material may be caused to flow in a second direction opposite to the first direction into the chamber 10, where the material is again acoustically treated, and flows in the second direction out of the chamber 10. Flow may be caused by one or more pumps, acoustic streaming, gravity and/or other motive forces. Also, acoustic treatment may be performed in a continuous manner, for extended periods of time (over 1 hour) with the acoustic energy source 2 operation at a power output of 200 watts or greater. As with other methods in accordance with the invention, various aspects may be combined together, such as chambers that include acoustic windows, chambers that include heat exchanger features, and so on.

Another method in accordance with the invention relates to treating material using a system like that in FIG. 8 or a similar system. For example, material may be caused to flow into a first chamber 10, the material is exposed to focused acoustic energy in the internal volume of the first chamber 10 (where the acoustic energy at a focal zone has the properties described herein), and the material is caused to flow out of the first chamber 10, and into a second chamber 10, where the material is again acoustically treated. Serial treatment of the material may be repeated with three or more chambers, and the treatment conditions may be the same, or different, in the different chambers 10. Acoustic treatment may be performed in a continuous manner, for extended periods of time (over 1 hour) with the acoustic energy source 2 operation at a power output of 200 watts or greater. As with other methods in accordance with the invention, various aspects may be combined together, such as chambers that include acoustic windows, chambers that include heat exchanger features, and so on.

Temperature, Cavitation, Particle Size, Solubility, and Pressure Management and Control.

Visual Monitoring of the Sample

Optical or video detection and analysis can be employed to optimize treatment of the sample. For example, in a suspension of biological tissue, the viscosity of the mixture can increase during treatment due to the diminution of the particles by the treatment and/or by the liberation of macromolecules into the solution. Video analysis of the sample during treatment allows an automated assessment of the mixing caused by the treatment protocol. The protocol may be modified during the treatment to promote greater mixing as a result of this assessment. The video data may be acquired and analyzed by the computer control system (i.e., part of the controller 20) that is controlling the treatment process. Other optical measurements such as spectral excitation, absorption, fluorescence, emission, and spectral analysis also can be used to monitor treatment of the sample, whether in the chamber 10 or in a flow path upstream or downstream of the chamber 10. A laser beam, for example, can be used for alignment and to indicate current sample position. In certain embodiments the visual or optical detection can be performed through a window in the reaction chamber. This window can be the upper or lower window of the chamber 10, a visual window integrated into the vessel side itself, or can be a window integrated into the transfer tubing or sample reservoir.

Temperature Control

Certain applications require that the Temperature of the sample being processed be managed and controlled during processing. For example, many biological samples should not be heated above 4 degrees C. during treatment. Other applications require that the samples be maintained at a certain elevated temperature during treatment. The ultrasound treatment protocol influences the sample temperature in several ways: the sample absorbs acoustic energy and converts it to heat; the sample treatment chamber absorbs acoustic energy and converts it to heat which, in turn, can heat the sample; and acoustic streaming develops within the sample treatment chamber and the coupling medium, forcing convective heat transfer between the sample treatment chamber and the coupling medium.

The acoustic waves or pulses can be used to regulate the temperature of the solutions in the treatment chamber. At low power, the acoustic energy produces a slow stirring without marked heating. Although energy is absorbed to induce the stirring, heat may be lost rapidly through the sides of the treatment chamber, resulting in a negligible equilibrium temperature increase in the sample. At higher energies, more energy is absorbed, and the temperature rises. The degree of rise per unit energy input can be influenced and/or controlled by several characteristics, including the degree of heat absorption by the sample or the treatment chamber and the rate of heat transfer from the treatment chamber to its surroundings (e.g., the coupling medium). Additionally, the treatment protocol may alternate a high-powered treatment interval, in which the desired effects are obtained, with a low power mixing interval, in which acoustic streaming and convection are achieved without significant heat generation. This convection may be used to promote efficient heat exchange or cooling.

The sample temperature may be required to remain within a given temperature range during a treatment procedure. Temperature can be monitored remotely by, for example, an infrared sensor. Temperature probes such as thermocouples may not be particularly well suited for all applications because the sound beam may interact with the thermocouple and generate an artificially high temperature in the vicinity of the probe. Temperature can be monitored by the same computer that controls acoustic waveform. The control responds to an error signal which is the difference between the measured actual temperature of the sample and the target temperature of the sample. The control algorithm can be as a hysteritic bang-bang controller, such as those in kitchen stoves, where, as an output of the control system, the acoustic energy is turned off when the actual temperature exceeds a first target temperature and turned on when the actual temperature falls below a second target temperature that is lower than the first target temperature. More complicated controllers can be implemented. For example, rather than simply turning the acoustic signal on and off, the acoustic signal could continuously be modulated proportionally to the error signal, for example, by varying the amplitude or the duty cycle, to provide finer temperature regulation.

In the application of a bang-bang control algorithm for a multiple sample format, once a maximum temperature value has been exceeded and the sonic energy is turned off for a particular sample, an alternative to waiting for the sample to cool below a selected temperature before turning the sonic energy on again, is to move on to the next sample, or increase the flow rate of new sample material into the treatment chamber. Another alternative is to switch to a predefined "cooling" waveform which promotes convection without adding significant heat to a particular sample, and synchronizing this cycle with the introduction of new sample material to the chamber.

Cavitation Control

In some applications, it can be preferable to treat the sample with as much energy as possible without causing cavitation. This result can be achieved by suppressing cavitation. Cavitation can be suppressed by pressurizing the treatment chamber above ambient, often known as "overpressure," to the point at which no negative pressure develops during the rarefaction phase of the acoustic wave. This suppression of cavitation is beneficial in applications such as cell transformation where the desired effect is to open cellular membranes while maintaining viable cells. In other applications it may be desirable to enhance cavitation. In these applications, a "negative" overpressure or vacuum can be applied to the region of the focal zone.

The control of cavitation in the sample also can be important during acoustic treatment processes. In some scenarios, the presence of small amounts of cavitation may be desirable to enhance biochemical processes; however, when large numbers of cavitation bubbles exist they can scatter sound before it reaches the target, effectively shielding the sample.

Cavitation can be detected by a variety of methods, including acoustic and optical methods. An example of acoustic detection is a passive cavitation detector (PCD) which includes an external transducer that detects acoustic emissions from cavitation bubbles. (That is, the PCD may be external to the chamber 10, e.g., the PCD may be located in the coupling medium 4.) The signal from the PCD can be filtered, for example using a peak detector followed by a low pass filter, and then input to a controlling computer (part of controller 20) as a measure of cavitation activity. The acoustic signal could be adjusted in ways similar to those described in the temperature control example to maintain cavitation activity at a desired level.

Overpressure: Increased pressure in the chamber 10 is one technique for controlling cavitation. Overpressure tends to remove cavitation nuclei and increases the energy level required to create cavitation. Motes in the fluid are strongly affected by overpressure and so cavitation in free-fluid is often dramatically reduced, even by the addition of one atmosphere of overpressure. Nucleation sites on the chamber 10 walls tend to be more resistant to overpressure; however the cavitation tends to be restricted to these sites and any gas bubbles that float free into the free-fluid are quickly dissolved. By increasing the ambient pressure of the system, the pressures required for bubble nucleation and collapse increase, thus increasing the force imparted by collapse of the cavitation bubble. This relationship is roughly linear—that is, doubling the ambient pressure of the system doubles the resulting force of bubble collapse. Careful system design to accommodate higher overall pressures can allow this to scale by many factors. Overpressure may be applied to the treatment chamber, an array of treatment chambers, the treatment coupling medium and vessel, or to the entire system to achieve a higher than atmospheric pressure in the region of the focal zone.

Degassing: Reducing the gas content of the material fluid tends to reduce cavitation, again by reducing cavitation nuclei and making it harder to initiate cavitation. Another method of controlling cavitation or the effects of cavitation is to control the gasses that are dissolved in the sample fluid. For instance, cavitation causes less mechanical damage in fluid saturated with helium gas than in fluid saturated with argon gas.

Monitoring of Cavitation

A variety of methods may be employed to detect cavitation. For example, acoustic emissions, optical scattering, high-speed photography, mechanical damage, and sonochemicals can be used. As described above for monitoring temperature, information from cavitation detection can be used by the system to produce an output that selectively controls exposure of a sample to sonic energy in response to the information. Each of these methods to monitor cavitation are described more fully below.

Acoustic emissions: Bubbles are effective scatterers of ultrasound. The pulsation mode of a bubble is referred to as monopole source, which is an effective acoustic source. For small, generally linear oscillations, the bubble simply scatters the incident acoustic pulse. However, as the response becomes more nonlinear, it also starts to emit signals at higher harmonics. When driven harder, the bubbles start to generate subharmonics as well. Eventually as the response becomes a periodic or chaotic, the scattered field tends towards white noise. In the scenario where inertial collapses occur, short acoustic pressure pulses are emitted. An acoustic transducer can be configured to detect these emissions. There is a detectable correlation between the onset of the emissions and cell disruption.

Optical scattering: Bubbles also scatter light. When bubbles are present, light is scattered. Light can normally be introduced into the system using fiber optic light sources so that cavitation can be detected in real-time, and therefore can be controlled by electronic and computer systems.

High-speed photography: Bubbles can be photographed. This method typically requires high-speed cameras and high intensity lighting, because the bubbles respond on the time frame of the acoustics. It also requires good optical access to the sample under study. This method can give detailed and accurate data and may be a consideration when designing systems according to the invention. Stroboscopic systems, which take images far less frequently, can often give similar qualitative performance more cheaply and easily than high-speed photography.

Mechanical damage: Cavitation is known to create damage to mechanical systems. Pitting of metal foils is a particularly common effect, and detection method. There is a correlation between the cavitation needed to pit foils and to disrupt cells.

Sonochemicals: A number of chemicals are known to be produced in response to cavitation. The yield of these chemicals can be used as a measure of cavitational activity. A common technique is to monitor light generation from chemicals, such as luminol, that generate light when exposed to cavitation. Sonochemical yield usually can not be done during cell experiments but can be done independently under identical conditions, and thereby, provide a calibrated standard.

Materials for Treatment

A. Biological Materials

Many biological materials can be treated according the present invention. For example, such materials for treatment include, without limitation, growing plant tissue such as root tips, meristem, and callus, bone, yeast and other microorganisms with tough cell walls, bacterial cells and/or cultures on agar plates or in growth media, stem or blood cells, hybridomas and other cells from immortalized cell lines, and embryos. Additionally, other biological materials, such as serum and protein preparations, can be treated with the processes of the invention, including sterilization.

B. Binding Materials

Many binding reactions can be enhanced with treatments according to the invention. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

C. Chemical and Mineral Materials

Organic and inorganic materials can be treated with controlled acoustic pulses according to the methods of the invention. The sonic pulses may be used to commute a solid material, particularly under a feedback control regime, or in arrays of multiple samples. As with biological samples, individual organic and inorganic samples in an array can be treated in substantial isolation from the laboratory environment. Beside altering their physical integrity, materials can be dissolved in solvent fluids, such as liquids and gasses, or extracted with solvents. For example, dissolution of polymers in solvents can be very slow without stirring, but stirring multiple samples with current methods is difficult and raises the possibility of cross-contamination between samples. However, stirring of multiple samples without cross-contamination between samples can be accomplished with apparatus and methods of the present invention.

Treatment Applications

A. Altering Cell Accessibility

Sonicators can disrupt cells using frequencies around 20 kHz. It is generally thought there are two ways in which ultrasound can affect cells, namely by heating and by cavitation, which is the interaction of the sound wave with small gas bubbles in the sample. Heating occurs primarily due to absorption of the sound energy by the medium or by the container. For dilute aqueous systems, it is absorption by the container that is a main source of the heating. Heating is not desirable in some treatment applications, as described herein. The heating associated with the compression and cooling associated with the rarefaction of a sound wave is relatively small, even for intense sound.

According to the invention, controlled sonic pulses in a medium are used to treat a sample containing biological material. The pulses can be specifically adapted to preferentially interact with supporting matrices in a biological material, such as plant cell walls or extracellular matrices such as bone or collagen, thereby lessening or removing a barrier function of such matrices and facilitating the insertion of extracellular components into a cell. In this application, the cell is minimally altered and cell viability is preserved. These pulses can be caused by shock waves or by sound waves. The waves can be created external to the sample, or directly in the sample, via applied mechanical devices. In experiments where thermal effects are negligible, there typically is no lysis, unless cavitation is present. Other modes of sonic energy can have different effects than disrupting a matrix and can be used either with pre-treatment, with disrupting sonic energy, or by themselves. For, example the conditions to disrupt a matrix can be different from those to permeabilize a cell membrane.

There are many possible mechanisms by which cavitation may affect cells and there is no consensus as to which mechanisms, if any, dominate. The principle mechanisms are thought to include shear, microjets, shock waves, sonochemistry, and other mechanisms.

B. Extracting

In a variation of the method to alter cellular accessibility described above, controlled pulses in a medium can be used to treat a sample containing biological material to extract a fraction or fractions of the biological material. The pulses are specifically adapted to preferentially interact with supporting matrices, such as plant cell walls or extracellular matrices such as bone or collagen, or materials having differences in rigidity or permeability in a biological material, thereby lessening or removing a barrier function of such matrices or materials. These pulses can be caused by shock waves or by sound waves. The waves can be created external to the sample, or directly in the sample, via applied mechanical means.

The supporting matrix of a biological sample can be disrupted without disrupting one or more selected internal structures of the cells contained within the matrix. Representative examples of such samples are: i) bone, in which a rigid matrix contains living cells of interest; ii) mammalian tissue samples, which contain living cells embedded in a matrix of elastic connective tissue and "glycocalyx" or intercellular matrix; and iii) plant tissues, such as leaves, which contain cells in a matrix of cellulose, often crosslinked with other materials, of moderate rigidity. Virtually all living cells are gelatinous in texture, and can be deformed to some extent without rupture or internal damage. Matrices, in contrast, are designed to support and protect cells, as well as to achieve other biological functions. In the three examples above, the matrices of bone and leaves are designed to provide rigidity to the structure, while the support of most collagenous matrices has a strongly elastic character. Thus, different protocols for example, amplitude, duration, number of pulses, and temperature of sample, may be used to disrupt different matrices by mechanical means without damaging the cellular material.

Three areas to optimize for extraction are treatment waveform, mixing waveform, and positioning or dithering. One method to determine the appropriate treatment and positioning parameters for a target sample for extraction purposes is described below.

First, a solid sample is placed in a volume of liquid in about a 1:1 ratio (weight/volume), in a treatment chamber. For example, 0.25 ml of methanol is added to 0.25 gm of leaf tissue in a 0.5 ml treatment chamber. A single sample is placed within the focal zone of the sonic apparatus. Without using the treatment protocol, the mixing waveform is adjusted to provide "stirring" of the sample at the lowest amplitude, fewest cycles/burst, and lowest duty cycle. After the mixing waveform protocol is defined, the disruption treatment waveform is adjusted by immobilizing the target sample in the focal zone such that there is no mixing and no sample movement, such as dithering. Using a sonic energy source such as a piezoelectric transducer, the sample is subjected to a minimum number of cycles per burst, for example, three. For extraction purposes, the amplitude is initially used with a nominal 500 mV setting. A portion of the sample is treated and inspected under a microscope for signs of membrane disruption. Such inspection can be done in conjunction with dyes that stain intracellular organelles. The number of cycles/burst is then increased until a particular desired tissue disruption level is achieved in the immobilized portion of tissue. With a fresh sample, and with a 1:1 ratio of tissue to liquid, the temperature of the sample is monitored during a million cycle total treatment with an infra-red sensor directed to the top of a thin polyethylene film covering the sample vessel. The duty cycle is adjusted to keep the temperature within predefined ranges, such as 4 degrees C. within +/−2 degrees C. As discussed above, the different phases of extraction can be performed with different treatment chambers arranged in series (as in FIG. 8) or with the same chamber (e.g., where material flows in an oscillating manner through the chamber 10). The different chambers, or treatment conditions, may be adjusted to achieve the desired result for each stage in the process.

C. Introducing a Molecule into or Removing a Molecule from a Cell

Once a sample having a matrix has been sufficiently weakened or attenuated, but not to the point where a substantial number of cells contained within the matrix are killed or lysed, an exposed target cell or cells become amenable to insertion of exogenous molecules by techniques such as transfection or transformation. With some matrices, it may be convenient to isolate the cells from the matrices and then to transfect the cells. In other cases, it will be preferable, particularly in an automated system, to perform the transfection directly on the treated tissue sample, using solutions and conditions adapted from known techniques. Alternatively, in situations where a cell to be treated is not situated within a matrix, the cell can be directly treated according to the process below without having to pre-treat the matrix. While the treatment below is described mainly for transfection, methods and apparatus according to the present invention are equally applicable to a transformation process or other processes to introduce an exogenous material into a permeabilized cell membrane.

The waveforms used to alter the permeability of a cell are refined depending on the particular application. Typically, the shock wave is characterized by a rapid shock front with a positive peak pressure, for example about 100 MPa, and a negative peak pressure, for example about negative 10 MPa. This waveform is of a few microsecond duration, on the order of about 5 microseconds. If the negative peak is greater than about 1 MPa, cavitation bubbles may form. Cavitation bubble formation is also dependent upon the surrounding medium. For example, glycerol is a cavitation inhibitive medium; whereas, liquid water is a cavitation promotive medium. The collapse of cavitation bubbles forms "microjets" and turbulence that impinge on the surrounding material.

Sound waves, namely acoustic waves at intensities below the shock threshold, provide an alternative means of disrupting the matrix to allow access to the plasma membranes of the cells to allow transformation. Such sound waves can be generated by any known process. As biological material is subjected to subzero temperatures, for example about negative 5 degrees C., most but not all of the water is in the solid phase. However, in certain biological tissues micro-domains of liquid water still remain for several reasons, such as natural "antifreeze" molecules or regions of higher salt concentration. Therefore, as a sample temperature is varied during the treatment with sound or shock waves, microdomains of liquid water are able to form shock waves and induce cavitation bubble formation and collapse, with the resultant shear stresses that impinge on surrounding tissues. Indeed, gradual alteration of the sample temperature can be desirable, as it provides focused domains of liquid water for impingement on the surrounding material. The waves can be applied to the samples either directly, as piezoelectric pulses, or via an intervening medium. This medium may be water, buffer, stabilizing medium for the target material be isolated, or extraction medium for the target. An intervening medium also can be a solid, formed of a material which is intrinsically solid, or of a frozen solution.

At that point, or, optionally, previously, a solution or suspension containing the material to be incorporated into the cells is added to the sample. In one embodiment, the exogenous material is incorporated into the cells in a conventional manner, as is known in the art for cells with exposed plasma membranes. In another embodiment, acoustic energy is used to transiently permeabilize a plasma membrane to facilitate introduction of exogenous materials into the cells. The exogenous material may be present in the sample during the weakening of the matrix by acoustic energy. Even when the cells remain intact, as determined by dye exclusion or other viability measurements, the process of weakening the cell matrix by acoustic energy transiently destabilizes the plasma membranes, increasing the uptake of exogenous macromolecules and structures. If a further increase in the rate of incorporation is needed, then the intensity or time of application of acoustic energy is slightly increased until the cell membrane becomes transiently permeable. For example, a gentle pulse or wave is applied to the mixture, with a predetermined amplitude. This amplitude can be determined readily in separate experiments on samples of the same type to transiently make a plasma membrane of a cell type porous, in a similar empirical manner to the steps described above for determining an appropriate treatment to disrupt a matrix. During the transient porous state, exogenous materials diffuse into the cell and the materials are trapped there once the sonic or shock pulse is removed.

A major advantage of these methods for transfection, or other incorporation of exogenous material into living cells, is that the methods are readily amenable to scale-up, to automation, and to marked reduction in sample size and reagent volume. Thus, the methods are adaptable to large scale automation, in large part because they do not require the isolation of the cells from their matrix. Additionally, these methods are amenable to a continuous flow process such as those described herein. For example, the sonic energy treatment can be different for permeabilization than for sterilization, but the sample to be treated can be flowed through an apparatus similar to that described in FIG. 6.

The number of cells per ml of media is also important factor for cellular applications to use acoustics effectively the concentration of the cells should not be too low (as the energy generated and utilized depends on the concentration of cells)

or too high (viscosity is high). Additionally, with the process of permeabilization and with the mixing profile, other techniques of gene transfer may be augmented. Examples include, calcium phosphate coprecipitation, electroporation, and receptor-dependent processes.

D. Sterilizing

The terms "sterilize," "disinfect," "preserve," decontaminate," "inactivation," "disinfect," and "kill" are used interchangeably herein, unless otherwise demanded by the context. "Sterilization," namely killing of all organisms, may not be synonymous in certain operations with "decontamination," for example, when the contaminant is non-living, such as a protein or prion. These terms, typically, mean the substantial elimination of or interference with any activity of a particular organism and/or particle.

Methods for permeabilization and extraction, described above, can be modified to sterilize a sample. The apparatus and methods for sterilizing can be optimized for efficient sterilization of particular materials in particular volumes and containers. For a particular material to be sterilized, an initial set of conditions is selected. Such conditions can include selection of a type of sonic pulse generator, intensity of sonic energy, frequency of sonic energy, where relevant, and/or like variables. The conditions also can include volume, mode of transport, and/or exposure of the materials to be sterilized. Then, the initial conditions and near variants are applied to the sample, and the percentage of cells or viruses killed is determined by standard assay conditions. Further variables are selected for change. Accordingly, a zone of maximal killing of the test organism is found. Finally, other variables, such as flow rate and/or length and/or intensity of sonic exposure, are optimized to provide both a technical solution and a commercially useful solution to the problem of sterilizing a particular material. Any of these empirically determined values can be programmed into a control system of an apparatus used for sterilization to actively control sterilization, or the apparatus can have these values previously determined such that a user need only select a predetermined sterilization mode an the apparatus.

For many liquids, adequate sterilization is provided by destroying the cell walls of bacteria, fungi, and other living cells. This result is accomplished by using frequencies and wavelengths of sound which preferentially excite the membranes of the cells while minimally heating the solution until the cells are lysed. In most cellular organisms, opening the membrane and allowing the contents to mix with an extracellular fluid will kill the organism.

Viruses can be opened to the solution by similar processing. In the case of viruses, exposure of their internal nucleic acid to the solution may not be adequate to completely inactivate them, since the naked DNA or RNA can also be infectious. Adjuncts such as iodine or nucleic-acid digesting enzymes in the solution can be provided to complete the inactivation of the viruses.

E. Mixing, Stirring, and Heating

In fluid samples, including powdered and granular media and gasses, sample mixing is conventionally performed by vortexing or stirring, or other methods such as inversion of a sample containing an air space, and shaking. Vortexing is essentially achieved by mechanical motion of the entire vessel while stirring involves mechanical contact of a driven device with a fluid. Stirring is accomplished with a variety of devices, for example with propellers, impellers, paddles, and magnetic stir bars. One problem with these methods is that it is difficult to increase their scale in order to handle dozens or hundreds of sample vessels at once. Another problem with these methods is the difficulty of mixing multiple samples while keeping the each sample substantially free from contamination. As described in more detail below, methods according to the invention can use sonic energy to mix a sample while avoiding problems with contamination. Factors, such as focusing the sonic energy, as well as otherwise controlling an acoustic waveform of the sonic energy, can be used to selectively mix a sample, for example, through acoustic streaming and/or microstreaming.

A fluid sample can be mixed controllably using the systems described herein. No direct contact between the material to be mixed and the sonic energy source is required. When the material to be mixed is in a treatment chamber, the treatment chamber itself is not necessarily touched by the source and is typically coupled to the source by a coupling medium.

F. Enhancing Reactions and Separations

In certain embodiments, temperature, mixing, or both can be controlled with ultrasonic energy to enhance a chemical reaction. For example, the association rate between a ligand present in a sample to be treated and an exogenously supplied binding partner can be accelerated. In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture. The temperature, mixing, or both, are changed from the initial condition to enhance ligand complex formation with an exogenously supplied binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand is reacted with the exogenously supplied binding partner.

Polymerase Chain Reaction ("PCR") Thermal Cycling

One of the bottlenecks of the PCR technique is cooling time. The heating cycle is rapid; however, cooling is limited by convection. Even in biochip formats, in which DNA or another target molecule is immobilized in an array on a microdevice, there is no "active" cooling process. However, certain embodiments of the invention can be used to overcome this bottleneck.

In certain embodiments, a treatment process can be used to both heat and cool the sample rapidly with little overshoot from a baseline temperature at which the primer and target to be amplified anneal. The process can be summarized as follows. A sample is treated with relatively high power sonic energy such that the sample absorbs sonic energy and is heated. Then, the sample is mixed at low power to cool the sample by forcing convection, which may be accomplished in conjunction with a cool water bath. The heating and cooling steps can be performed in the same chamber 10, or alternately in separate chambers 10, e.g., in a system like that in FIG. 8. The material can be controlled by the timing of the transfer mechanism, such as the pump, to allow discrete processing times 'in chamber' before discharging the material and bringing in new material. This can provide time for process steps such as processing, mixing, cooling and others to fully develop before introducing new unprocessed sample to the chamber.

G. Purification, Separation, and Reaction Control

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations.

Sonic fields also can be used to minimize concentration polarization in membrane processes, including particle classification, filtration of fine particles and colloids, ultrafiltration, reverse osmosis, and similar processes. Concentration polarization is the result of the tendency of filtered material to be present at high concentration in a layer on the filter. This layer has a low fluid concentration and, thus, diminishes the rate of filtration as the filtered solution becomes more concentrated, or as the layer thickens. This layer can be stirred remotely by focused sonic energy of low to moderate intensity. Flow rate, thus, can be enhanced without significant cost in energy or membrane life.

H. Further Uses for Remotely Actuated and Controlled Solution Mixing with Sonic Energy Control of sonic energy emission, sonic energy characteristics, and/or location of a target relative to sonic energy also can be used to pump and control the flow rate of liquids, especially in capillaries; enhance chemical reactions, such as enhancing second-order reaction rates; increase effective Reynolds number in fluid flow; and control the dispensing of semi-solid substances.

By focusing sonic energy and positioning it near a wall of a chamber or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common.

The controller 20 may include any suitable components to perform desired control, communication and/or other functions as described above. For example, the controller 20 may include one or more general purpose computers, a network of computers, one or more microprocessors, etc., for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the acoustic energy source 2, a pump 33, etc., as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the material in a chamber 10, a video camera or other imaging device to capture and analyze image information regarding the chamber 10 or other components, position sensors to indicate positions of the acoustic transducer 2 and/or the vessel 10, and so on), user data input devices (such as buttons, dials, knobs, a keyboard, a touch screen or other), information display devices (such as an LCD display, indicator lights, a printer, etc.), and/or other components for providing desired input/output and control functions.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A system for acoustically treating a material, comprising:
a chamber including an internal volume having a tapered shape configured to interact with acoustic energy emitted into the internal volume;
a substantially flat acoustic energy source constructed and arranged to emit unfocused acoustic energy having a frequency of about 100 kHz to 100 MHz toward the chamber; and
an acoustic lens or acoustically reflective surface arranged to focus the unfocused acoustic energy of the acoustic energy source to form a focal zone of acoustic energy located at least partially within the internal volume, wherein the shape of the internal volume of the chamber tapers from an acoustic energy source end of the internal volume toward a focal zone end of the internal volume, the acoustic energy source end located opposite the focal zone end.

2. The system of claim 1, wherein the shape of the internal volume of the chamber comprises a conical, frustoconical, or curved portion.

3. The system of claim 1, wherein the shape of the internal volume of the chamber is tapered such that a cross-sectional area of the volume closer to the acoustic energy source is larger than a size of the cross-sectional area of the volume farther away from the acoustic energy source.

4. The system of claim 1, wherein the shape of the internal volume of the chamber flares outwardly in a direction toward the acoustic energy source.

5. The system of claim 1, wherein the shape of the internal volume is downwardly flaring.

6. The system of claim 1, wherein the chamber comprises the acoustic lens or acoustically reflective surface.

7. The system of claim 1, wherein the chamber comprises one or more insert elements defining the shape of the internal volume of the chamber.

8. The system of claim 7, wherein the one or more insert elements comprises a sleeve arrangement.

9. The system of claim 8, wherein the sleeve arrangement comprises an outer cylindrical shape and an inner conical or frustoconical shape.

10. The system of claim 7, wherein the one or more insert elements comprises a single component, or two or more separate parts.

11. The system of claim 7, wherein the one or more insert elements comprises a surface having a plurality of nucleation features.

12. The system of claim 7, wherein the one or more insert elements comprises a ceramic material.

13. The system of claim 1, further comprising a plurality of nucleation features configured to be suspended in the internal volume of the chamber when subject to acoustic processing.

14. The system of claim 1, wherein the acoustic lens comprises a window configured to transmit emitted acoustic energy into the internal volume of the chamber.

15. The system of claim 14, wherein the window is constructed and arranged to cause convergence of the emitted acoustic energy.

16. The system of claim 1, wherein the acoustically reflective surface comprises an acoustic mirror constructed and arranged to cause convergence of the emitted acoustic energy.

17. The system of claim 16, wherein the acoustic mirror is shaped to reflect the acoustic energy vertically and focus the acoustic energy into a converging beam.

18. The system of claim 1, wherein the focal zone of acoustic energy has a width of less than about 2 cm.

19. The system of claim 1, further comprising a coupling medium arranged to transmit acoustic energy from the acoustic energy source into the internal volume of the chamber.

20. The system of claim 1, wherein the tapered shape of the internal volume of the chamber is configured to re-direct the acoustic energy to form the focal zone of acoustic energy.

21. The system of claim 1, wherein the acoustic energy source is attached to the chamber.

22. A method of treating a material with acoustic energy, comprising:
    emitting unfocused acoustic energy having a frequency of about 100 kHz to 100 MHz from a substantially flat acoustic energy source into an internal volume of a chamber, the chamber including an internal volume having a tapered shape configured to interact with the emitted acoustic energy; and
    focusing the emitted acoustic energy to form a focal zone of acoustic energy located at least partially within the internal volume, wherein the shape of the internal volume of the chamber tapers from an acoustic energy source end of the internal volume toward a focal zone end of the internal volume, the acoustic energy source end located opposite the focal zone end.

23. The method of claim 22, wherein the shape of the internal volume of the chamber comprises a conical, frusto-conical, or curved portion.

24. The method of claim 22, wherein focusing the emitted acoustic energy comprises causing convergence of the acoustic energy by an acoustic lens or acoustically reflective surface.

25. The method of claim 24, wherein focusing the emitted acoustic energy comprises transmitting the emitted acoustic energy through an acoustic lens.

26. The method of claim 24, wherein focusing the emitted acoustic energy comprises reflecting the emitted acoustic energy off an acoustic mirror.

27. The method of claim 22, wherein the chamber comprises one or more insert elements defining the shape of the internal volume of the chamber.

28. The method of claim 22, wherein focusing the emitted acoustic energy comprises forming the focal zone of acoustic energy to have a width of less than about 2 cm.

29. The method of claim 22, further comprising transmitting the emitted acoustic energy from the acoustic energy source through a coupling medium into the internal volume of the chamber.

* * * * *